US011406792B2

(12) United States Patent
Ren et al.

(10) Patent No.: US 11,406,792 B2
(45) Date of Patent: *Aug. 9, 2022

(54) ANTIFOULING URINARY CATHETERS WITH SHAPE-MEMORY TOPOGRAPHIC PATTERNS

(71) Applicants: Dacheng Ren, Manlius (CN); Huan Gu, Syracuse (CN)

(72) Inventors: Dacheng Ren, Manlius (CN); Huan Gu, Syracuse (CN)

(73) Assignee: Syracuse University, Syracuse, NY (US)

( * ) Notice: Subject to any disclaimer, the term of this patent is extended or adjusted under 35 U.S.C. 154(b) by 409 days.

This patent is subject to a terminal disclaimer.

(21) Appl. No.: 16/674,199

(22) Filed: Nov. 5, 2019

(65) Prior Publication Data
US 2020/0078552 A1 Mar. 12, 2020

Related U.S. Application Data

(63) Continuation of application No. 15/255,241, filed on Sep. 2, 2016, now Pat. No. 10,500,370.
(Continued)

(51) Int. Cl.
*A61M 25/00* (2006.01)
*A61L 29/04* (2006.01)
*A61L 29/14* (2006.01)

(52) U.S. Cl.
CPC ....... *A61M 25/0017* (2013.01); *A61L 29/041* (2013.01); *A61L 29/14* (2013.01);
(Continued)

(58) Field of Classification Search
CPC ..... B81C 1/00134; B81C 1/0019; B63B 1/36; Y10T 428/24355; Y10T 428/24612; Y10T 428/24149; Y10T 428/24479; Y10T 428/24132; Y10T 428/24165; Y10T 428/24942; Y10T 428/24669; Y10T 428/24678; Y10T 428/24686; Y10T 428/24694; Y10T 428/24702; Y10T 428/24711; Y10T 428/24719; Y10T 428/24727; B82Y 30/00; A61L 2400/16
See application file for complete search history.

(56) References Cited

U.S. PATENT DOCUMENTS

| | | | | |
|---|---|---|---|---|
| 5,889,118 A | * | 3/1999 | Delgado | C08F 265/04 525/218 |
| 2005/0178286 A1 | * | 8/2005 | Bohn, Jr. | B81C 1/00206 428/323 |

(Continued)

*Primary Examiner* — Adam Marcetich
(74) *Attorney, Agent, or Firm* — Bond Schoeneck and King PLLC; David Nocilly

(57) ABSTRACT

A system of topographic patterns for the prevention of bacterial adhesion and biofilm formation. The patterns may be provided on the surfaces of certain devices that are prone to bacterial adhesion and biofilm formation, such as urinary catheters. To reduce bacterial adhesion and biofilm formation, and to remove existing biofilms, the patterns are induced to transform from a first topography to a second topography. For example, the surface patterns may be formed from a shape memory polymer and then heated to transform the patterns from the first topography to the second topography to dislodge bacteria and prevent fouling.

12 Claims, 18 Drawing Sheets

Related U.S. Application Data

Figures 1A, 1B, 1C, 1D, 1E:
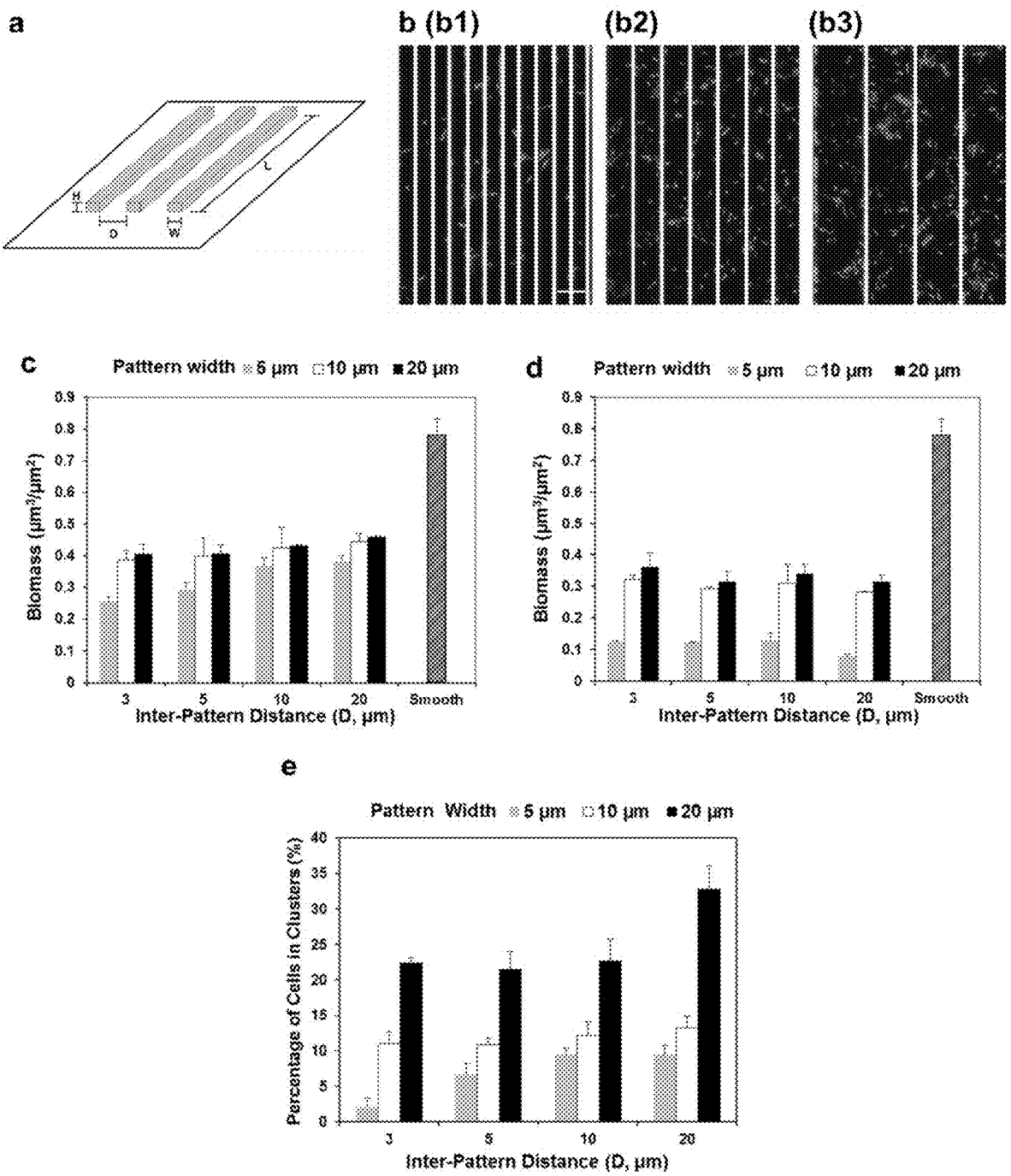

(60) Provisional application No. 62/213,338, filed on Sep. 2, 2015.

(52) U.S. Cl.
CPC .... *A61L 2400/16* (2013.01); *A61M 2025/006* (2013.01); *A61M 2025/0056* (2013.01); *A61M 2025/0058* (2013.01)

(56) References Cited

U.S. PATENT DOCUMENTS

| | | | |
|---|---|---|---|
| 2008/0023890 A1* | 1/2008 | Sherman | B29C 59/18 264/650 |
| 2008/0027199 A1* | 1/2008 | Mazurek | A61L 15/26 528/10 |
| 2009/0274877 A1* | 11/2009 | Chan | B32B 33/00 428/167 |
| 2010/0226943 A1* | 9/2010 | Brennan | B08B 17/06 428/141 |
| 2012/0058302 A1* | 3/2012 | Eggenspieler | B01D 65/08 428/689 |
| 2012/0232648 A1* | 9/2012 | Kahook | B29C 61/003 623/6.11 |
| 2012/0276334 A1* | 11/2012 | Fedynyshyn | B05D 5/08 264/293 |
| 2014/0030487 A1* | 1/2014 | Boyce | B32B 27/06 428/161 |
| 2014/0328999 A1* | 11/2014 | Aizenberg | B05D 3/06 427/547 |
| 2015/0159067 A1* | 6/2015 | Pesika | B81C 1/00103 264/129 |
| 2016/0114883 A1* | 4/2016 | Guerry | B81B 7/04 428/141 |
| 2016/0207083 A1* | 7/2016 | Kim | B05D 5/08 |
| 2017/0216543 A1* | 8/2017 | Magin | F28F 1/00 |

* cited by examiner

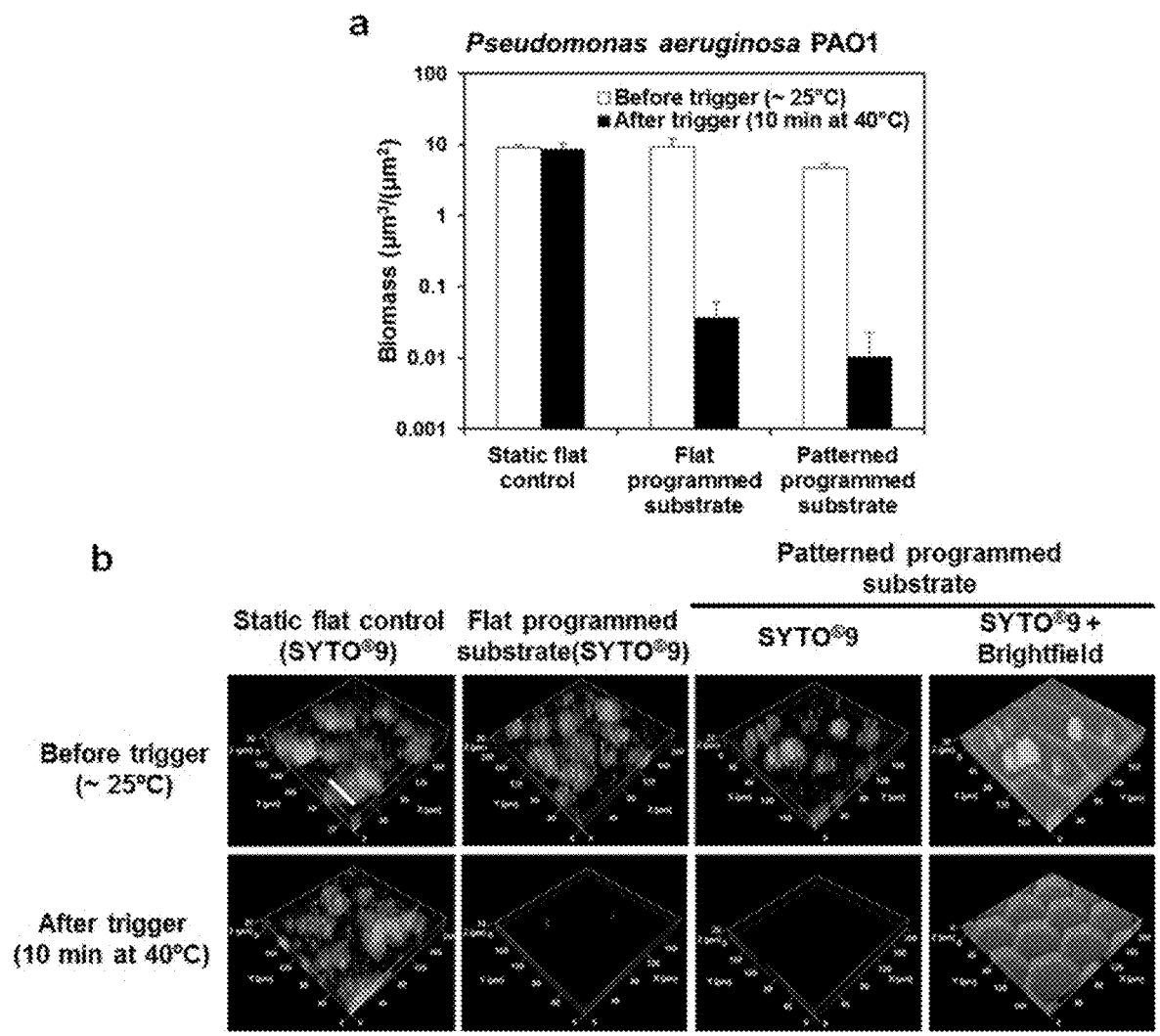
FIGS. 16(a) through (b)

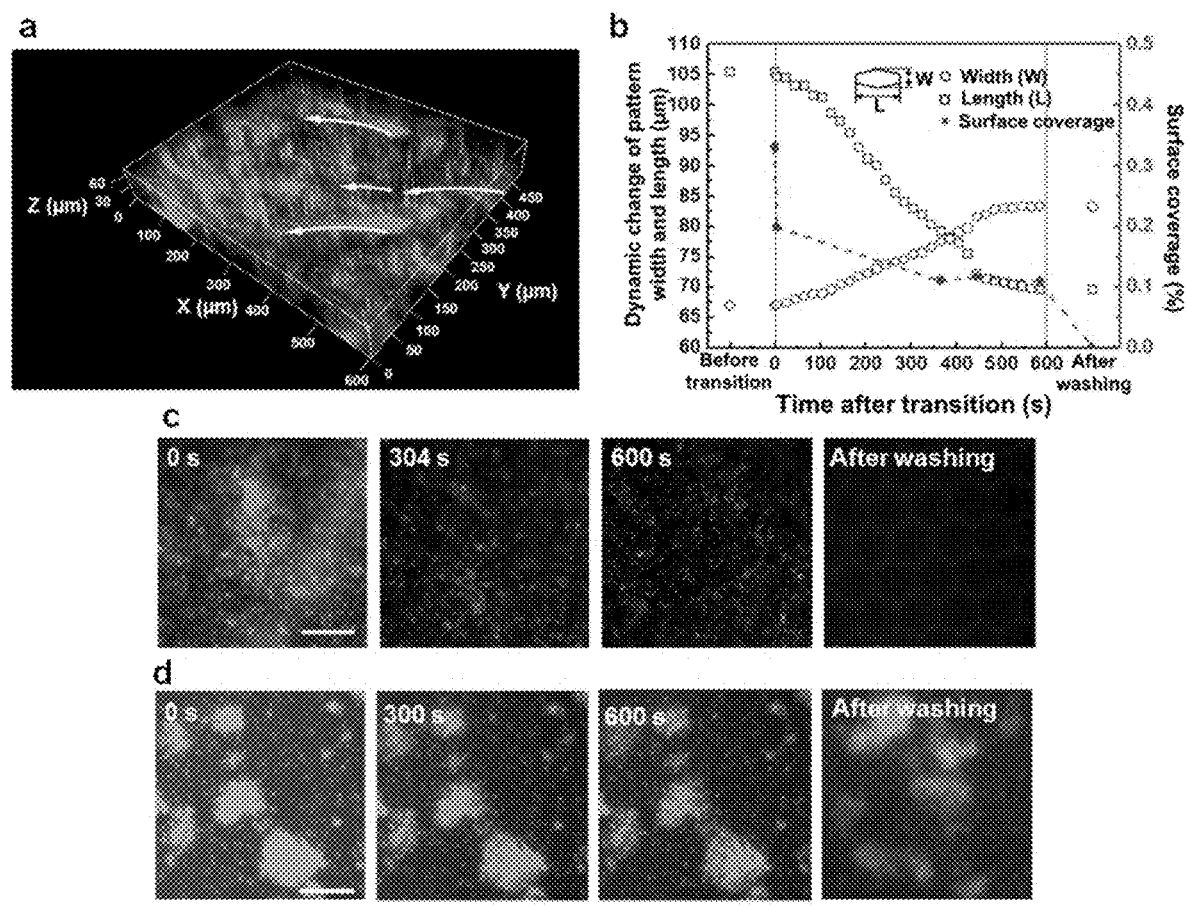
FIGS. 17(a) through (d)

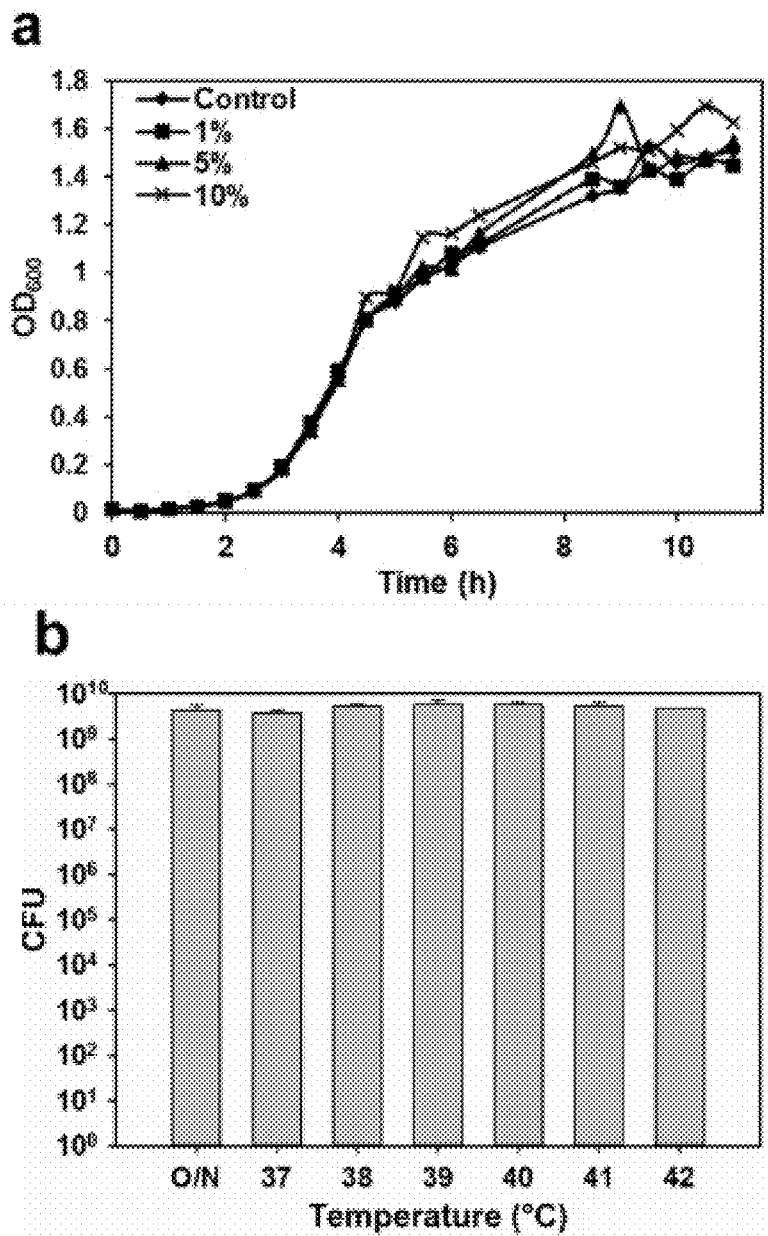
FIGS. 18(a) and (b)

ANTIFOULING URINARY CATHETERS WITH SHAPE-MEMORY TOPOGRAPHIC PATTERNS

CROSS-REFERENCE TO RELATED APPLICATIONS

The present application is a continuation of U.S. application Ser. No. 15/255,241, filed on Sep. 2, 2016, which claimed priority to U.S. Provisional No. 62/213,338, filed on Sep. 2, 2015.

STATEMENT REGARDING FEDERALLY SPONSORED RESEARCH OR DEVELOPMENT

This invention was made with government support under CAREER-1055644 and EFRI-1137186 awarded by the U.S. National Science Foundation. The government has certain rights in the invention.

BACKGROUND OF THE INVENTION

1. Field of the Invention

The present invention relates to medical devices and, more particularly, to topographic surfaces for medical devices such as catheters that prevent bacterial fouling.

2. Description of the Related Art

Bacteria have remarkable capabilities to attach to both biotic and abiotic surfaces and form multicellular structures with cells embedded in polymeric substances. Such complex sessile communities are known as biofilms and are found ubiquitously in aqueous environments. Biofilms are up to 1,000 times more resistant to antimicrobial agents than planktonic (free-swimming) bacteria of the same genotype. These multicellular structures are involved in 80% of bacterial infections in humans and play an important role in the spread of antimicrobial resistance due to biofilm-associated horizontal gene transfer. As a result, biofilms are a major cause of chronic infections and responsible for 99,000 deaths and 28-45 billion dollars of healthcare cost in the U.S. annually. Common medical devices such as catheters, prosthetic heart valves, joint prostheses, cardiac pacemakers, and many others are all at risk of biofilm infections. Due to the significance of biofilms, effective strategies for biofilm prevention and removal are urgently needed.

Catheters are one of the most widely used medical devices, and are frequently used for urine retention on an intermittent or indwelling basis. Urinary tract infections account for around 40% of noscomial infections, the majority of which are catheter-associated urinary tract infections (CAUTIs). The recent US multistate point-prevalence survey of healthcare-associated infections revealed that urinary tract infections (UTIs) are the fourth most common infection, and 67.7% of UTI patients had a urinary catheter. Despite the prevalence, the National and State Healthcare-associated Infections Progress Report published by CDC in 2014 also revealed an alarming 3% increase in CAUTI cases between 2009 and 2012.

Controlling nosocomial infections is challenging due to the compromised immunity among hospitalized patients and increased prevalence of drug resistant bacteria. Thus, novel devices and materials for effective control and prevention of nosocomial infections are acutely needed for life saving and recovery of infected individuals. This is also important for preventing the spread of multidrug resistant bacteria to the general public.

CAUTI occurs when an urinary catheter is not inserted or cleaned properly, left in the patient for too long, or not monitored correctly, leading to exposure to microbes which travel through the catheter by motility and cause infection of the patient. The most common microbial species involved in CAUTIs are *Escherichia coli, Candida* spp, *Enterococcus* spp, *Pseudomonas aeruginosa, Klebsiella pneumonia, Enterobacter* spp, *Proteus mirabilis,* and *Staphylococcus* spp. Bacteria establish infections by adhering to the catheter with flagella, pili, and adhesions. Attachment of bacteria leads to the subsequent formation of biofilms, which are surface-attached multicellular structures formed by microbes comprised of an extracellular matrix secreted by the attached cells. For example, the urease-forming bacterium *P. mirabilis* can form an extensive biofilm generating ammonia from urea and elevating the pH of urine. Due to rise in pH, crystals of calcium and magnesium phosphates precipitate in the urine and the catheter biofilm. This crystalline biofilm poses even further damage by initiating stone formation and septicaemia. Thus, in addition to the impact on quality of life, CAUTIs also cause a heavy financial burden on the health care system due to increase in treatment time and length of hospital stay.

Biofilms are difficult to treat due to extremely high tolerance of biofilm cells to antimicrobials and disinfectants (up to 1000 times higher compared to their planktonic counterparts). The close contact between biofilm cells also provides an ideal condition for bacterial horizontal gene transfer through conjugation, a process that mobile DNA elements carrying drug resistance genes are transferred between different bacterial species, leading to the emergence of multidrug resistant bacteria including "superbugs". Thus, it is extremely important to develop new control methods to prevent biofilm formation on indwelling medical devices.

Although biofilm formation has been extensively studied, biofilm control is still challenging. It is well known that biofilm formation is a dynamic process including attachment, microcolony formation, maturation, and dispersion (FIG. 1).

Recent research has shown that biofilm formation can be influenced by many factors of the substratum surface such as surface chemistry, topography, hydrophobicity, and charge. As an important surface property, surface roughness plays important roles in microbial adhesion and biofilm formation. However, the exact effects of surface roughness on bacterial adhesion and biofilm formation vary with the size and shape of bacterial cells and other environmental factors. Increasing data have shown that the conventional definition of roughness based on the average amplitude of peaks and valleys is not sufficient to describe the 3D feature of a surface and the distribution of peaks and valleys is also important to microbial biofilm formation. Recent advancements in material and surface engineering have brought exciting opportunities to create surfaces with not only controlled overall roughness, but also well-defined topographic patterns to control biofilm formation. In addition to the well-known example of Sharklet surfaces (with microscale topographic patterns inspired by the skin of shark), a number of µm- and nm-scale topographic patterns with varying shape and size have been shown to inhibit biofilm formation compared to flat surfaces of the same material, such as protruding and receding squares, circles, and parallel channels on polydimethylsiloxane (PDMS), cone-shaped patterns of silicone, ridges on PDMS, strain-induced wrinkles on PDMS, and circular poles on polystyrene. Some well-defined nanostructures can also lead to superhydrophobicity (Cassie state) and reduce biofouling. Despite the promise, how bacteria respond to surface topography is still poorly understood. As a result, the currently available topographic surfaces are largely based on empirical tests rather than rational design, lack of long-term activities, and are difficult to apply to catheter manufacturing. Thus, there is a need in the art for surface topographies that are designed to resist bacterial adhesions and biofilm formation in devices such as urinary catheters.

BRIEF SUMMARY OF THE INVENTION

The present invention comprises surface topographies that may be used to provide antifouling surfaces where bacterial biofilm formation otherwise presents a problem. For example, a medical device may be provided with a surface that can transform from a first topography to a second topography that is different than said first topography. The surface is formed from a shape memory polymer and transforms from said first topography to said second topography in response to a trigger, such as heat. For a catheter, the surface is provided on the inside of a catheter. The shape memory polymer can comprises t-butyl acrylate (tBA), poly (ethylene glycol)n dimethacrylate (PEGDMA), and photoinitiator 2,2-dimethoxy-2-phenylacetophenone (DMPA), or blends thereof. The first topography can comprise a linear pattern, or it can be a hexagonal pattern.

The present invention also includes a method of protecting against biofilm and bacterial adhesion by providing a medical device having a surface that can transform from a first topography to a second topography that is different than said first topography and then triggering the transformation from the first topography to the second topography to dislodge any bacterial. The surface comprises a shape memory polymer that transforms from said first topography to said second topography in response to a stimulus such as heat.

The role of μm scale surface topography changes according to the present invention was investigated in bacterial adhesion and cell cluster formation using polydimethylsiloxane (PDMS) surfaces modified with 5 μm tall line patterns and *Escherichia* coli as a model system. Compared with the smooth PDMS, the total biomass of 24 h biofilms formed on PDMS surfaces modified with 5 μm wide patterns (with 3 μm inter-pattern distance) and that on top of the line patterns was reduced by 62% and 85%, respectively. Cell cluster formation on top of the 5 μm wide patterns with 3 μm inter-pattern distance was reduce by 14-fold compared with that on the smooth PDMS. Interestingly, the attached *E. coli* cells were found to land more perpendicularly to the orientation of line patterns when the pattern width got narrower; and the mutants of fliC, motB, and fimA exhibited defects in such adjustment. In addition to the differences in attachment and cell cluster formation, the cells attached on narrow lines were found to be longer with higher transcriptional activities than those on wide line patterns.

Similarly, the present invention was also investigated using biocompatible shape memory polymers with defined surface topography. These surfaces can both prevent bacterial adhesion and remove established biofilms upon rapid shape change with moderate increase of temperature, thereby offering more prolonged antifouling properties. The approach of the present invention achieved a total reduction of *Pseudomonas aeruginosa* biofilms by 99.9% compared to the static flat control, and was also found effective against biofilms of *Staphylococcus aureus* and an uropathogenic strain of *Escherichia coli*.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIGS. 1(a) through (e) are a series of graphs showing surface coverage and cluster formation of the WT *E. coli* on patterns with varying pattern width (5, 10, or 20 μm) and inter-pattern distance (3, 5, 10, or 20 μm). FIG. 1(a) is a schematic description of PDMS line patterns used in this study. Pattern Length (L) and Height (H) were fixed at 4 mm and 5 μm respectively, while pattern width (W) and inter-pattern distance (D) were varied. FIG. 1(b) is a representative fluorescence images of WT *E. coli* cells attached to line patterns with 3 μm inter-pattern distance (D) and pattern width of 5 μm (b1), 10 μm (b2), or 20 μm (b3). Edges of patterns are labeled with white lines. FIG. 1(c) Total biomass of biofilm on PDMS modified with line patterns. FIG. 1(d) is a graph of biomass of biofilm on top of line patterns. FIG. 1(e) is a graph of cluster formation. Standard errors are shown. The area of valleys was covered with white bars for easy visualization of cells on top of line patterns.

FIG. 2(a) through 2(d) are a series of graphs showing: the orientation of the WT *E. coli* cells attached on PDMS line patterns. (a) Definition of cell orientation. (b, c, and d) Distribution of cell orientations on top of narrow (5 μm wide), medium (10 μm wide), and wide (20 μm wide) PDMS line patterns (mean±standard error).

Figure 3:
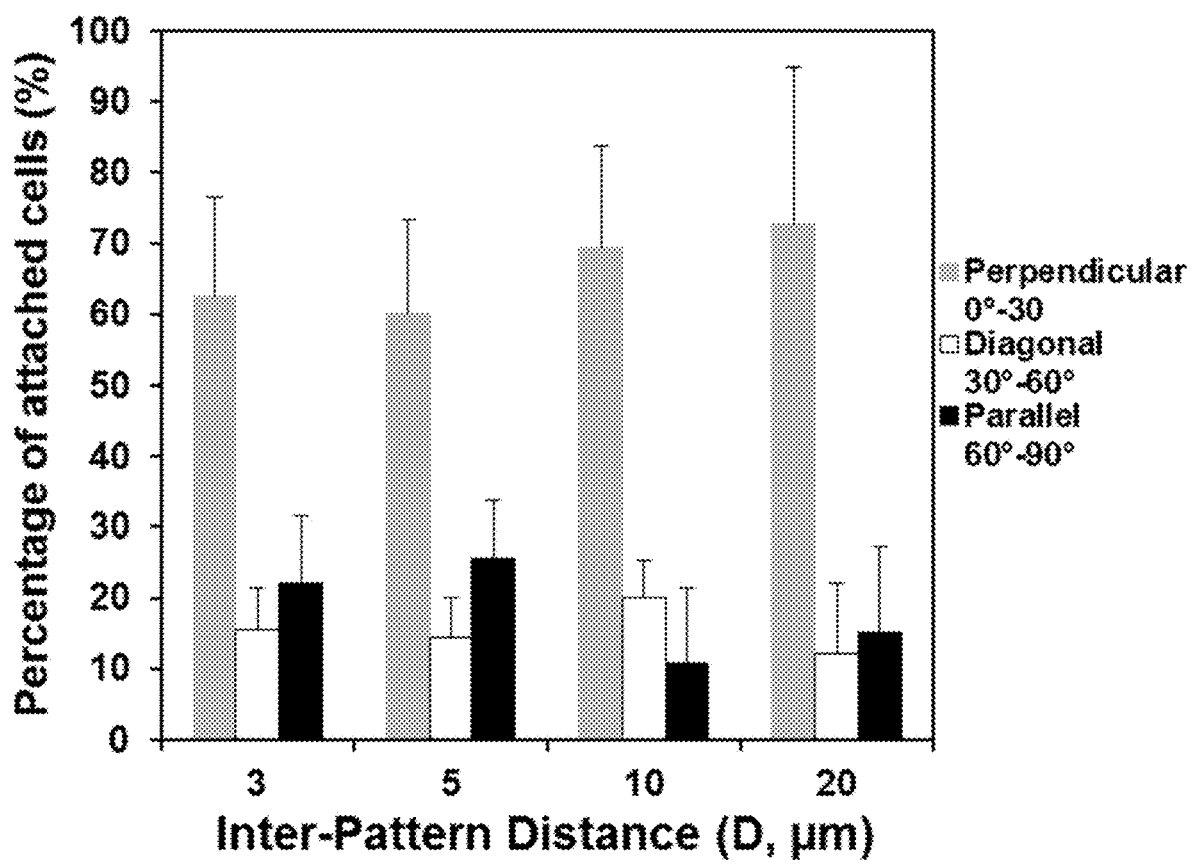

FIG. 3 is a graph showing the orientation of WT *E. coli* cells on top of 5 μm wide line patterns after 2 h of attachment (mean±standard error).

Figure 4:
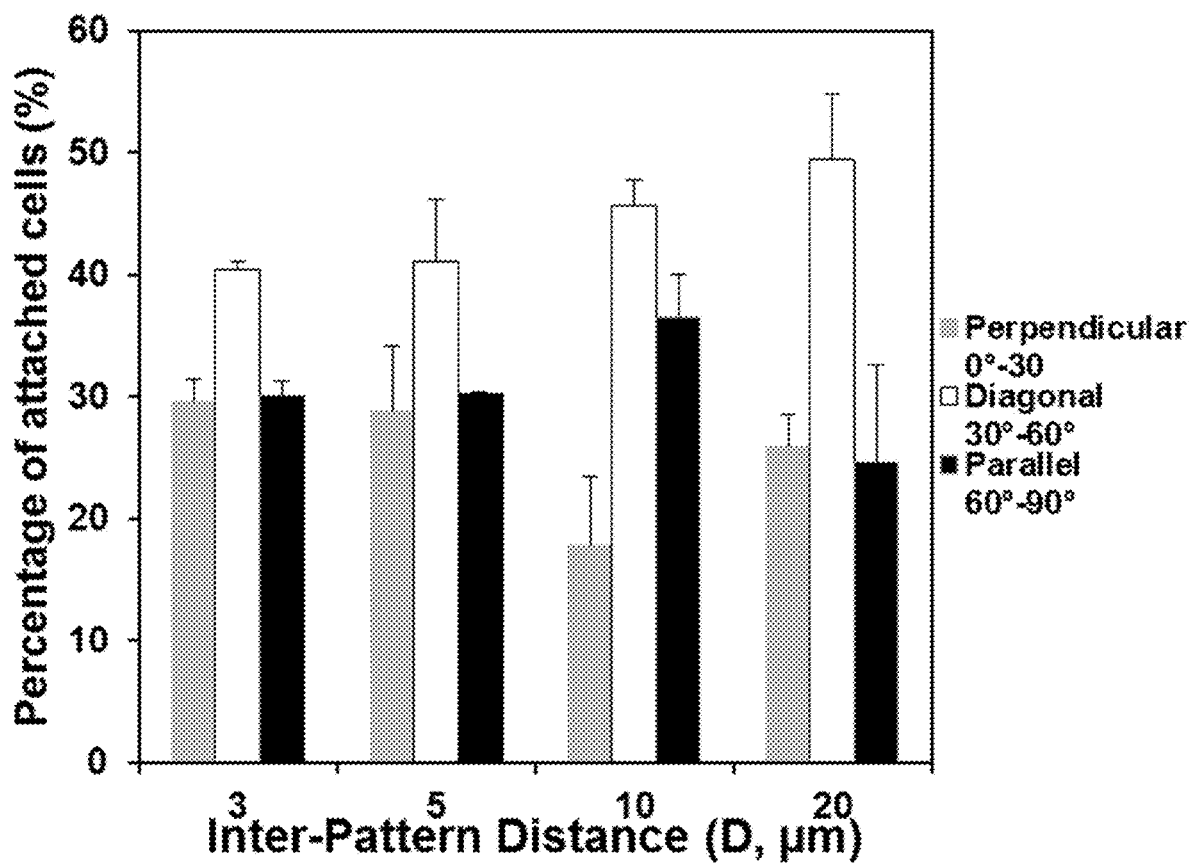

FIG. 4 is a graph showing the orientation of immobilized WT *E. coli* cells on top of 5 μm wide line patterns after 24 h biofilm culturing (mean±standard error). Seeding cells were pretreated with 10 μg/mL chloramphenicol for 1 h before inoculation.

Figures 5A, 5B, 5C, 5D:
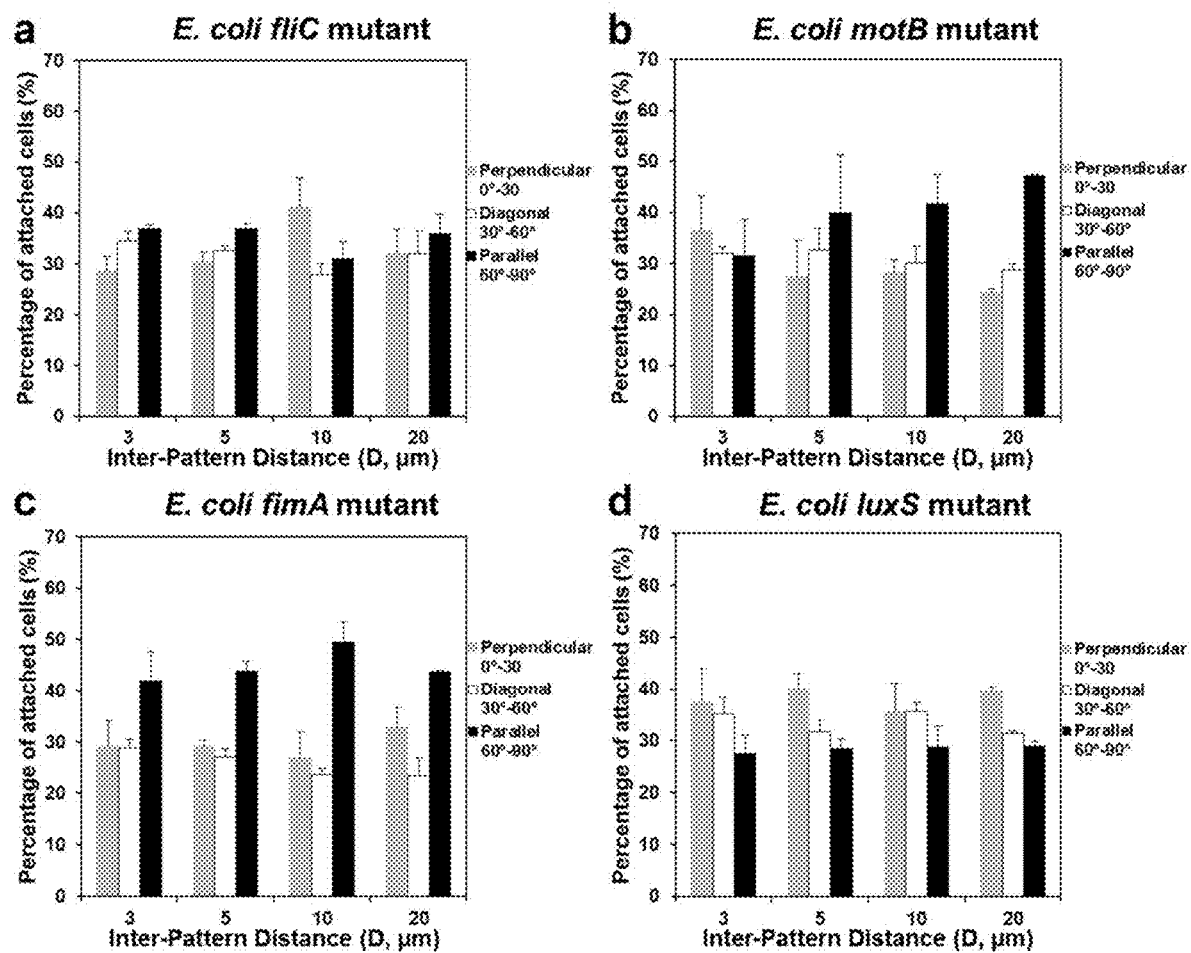

FIGS. 5(a) through 5(d) are a series of graphs showing: the orientation of isogenic mutant cells on top of 5 μm wide line patterns (mean±standard error). FIG. 5(a) ΔfliC mutant (*E. coli* RHG01/pRSH103), FIG. 5(b) motB mutant (*E. coli* RP3087/pRSH103), FIG. 5(c) ΔfimA mutant (*E. coli* RHG02/pRSH103), FIG. 5(d) ΔluxS mutant (*E. coli* KX1485/pRSH103).

Figure 6:
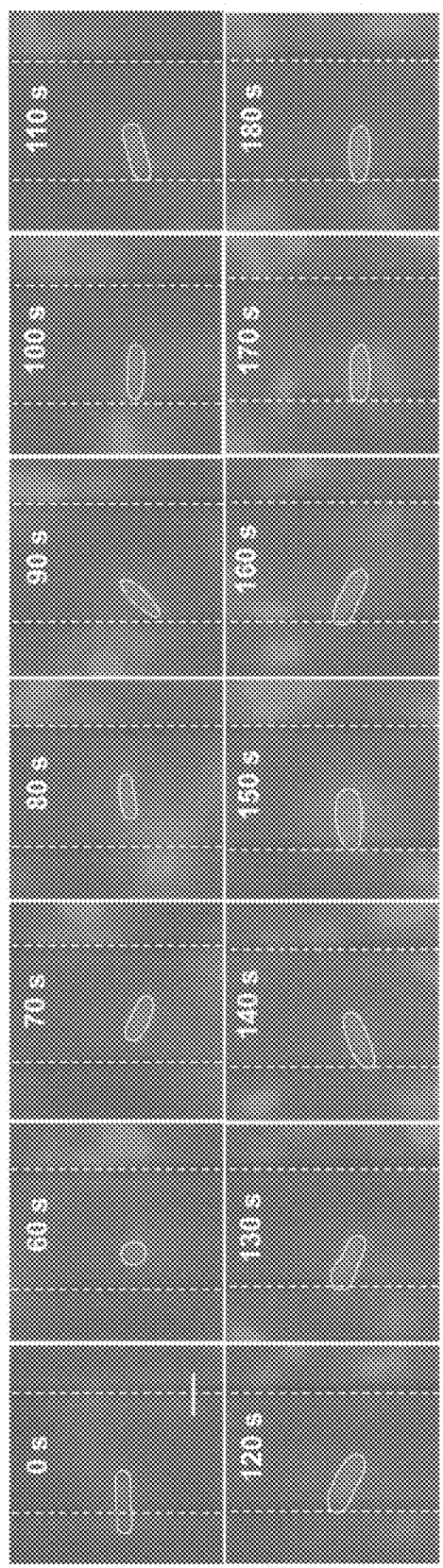

FIG. 6 is a series of time-lapse images of a representative WT *E. coli* cell after initial attachment. The cell spun after it landed on top of a line pattern and then settled after 3 min (Bar=2 μm). The cell body is highlighted with yellow line and the edges of the protruding line patterns were labeled with white dotted line.

Figures 7A, 7B, 7C:
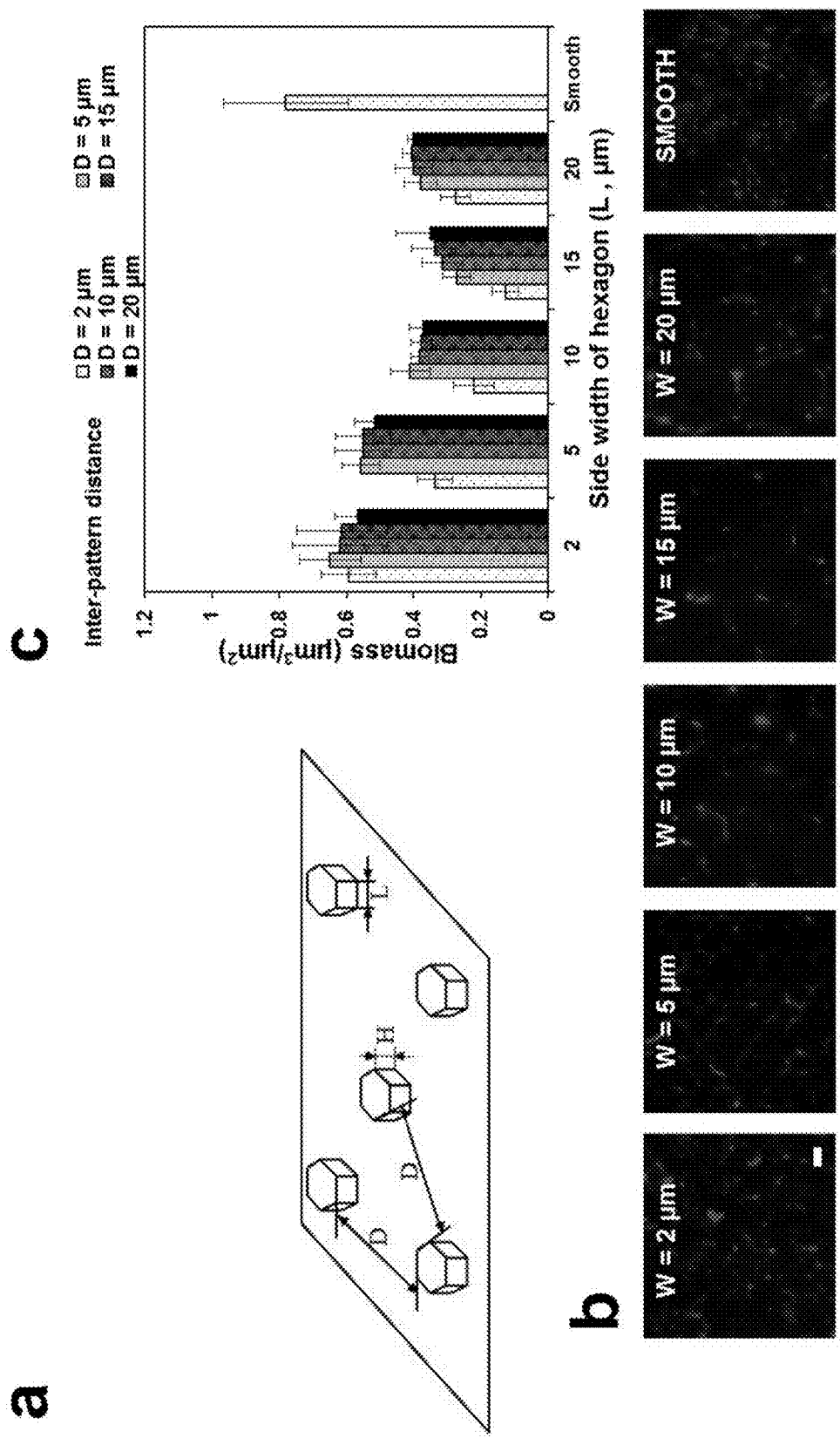

FIGS. 7(a) through 7(c) are a series of graphs and images showing: biofilm formation on surfaces modified with hexagon shaped patterns. FIG. 7(a) Schematic demonstration of the hexagon shaped patterns. FIG. 7(b) Representative pictures of the biofilms on PDMS surfaces modified with hexagon shaped patterns with side length of 2, 5, 10, and 20 μm and smooth PDMS surface. FIG. 7(c) Biomass of the WT *E. coli* biofilms on PDMS surfaces modified with hexagon shaped patterns with side length of 2, 5, 10, and 20 μm and inter-pattern distance of 2, 5, 10, 15, and 20 2, 5, 10, and 20 μm.

Figures 8A, 8B:
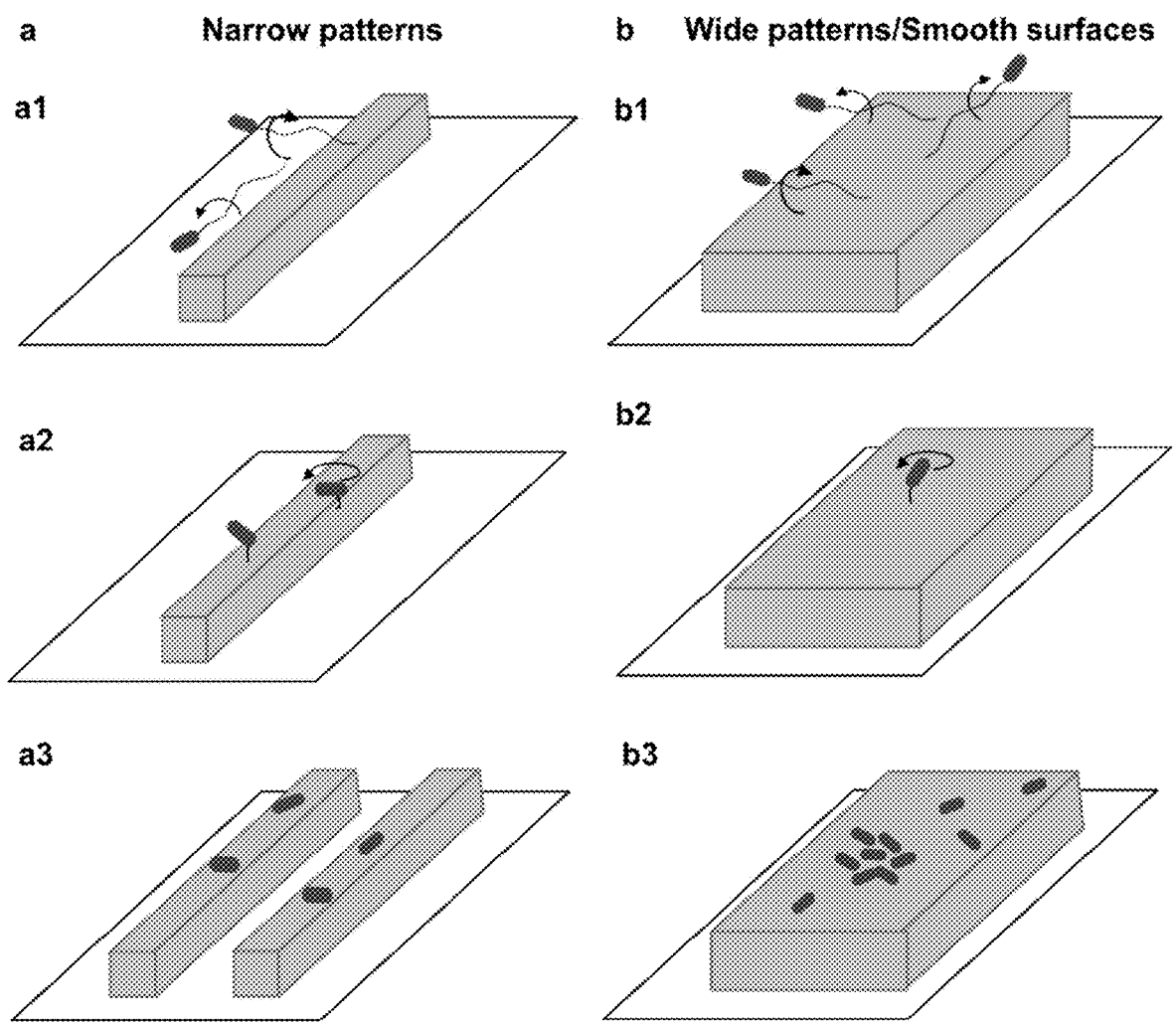

FIGS. 8(a) and 8(b) are a series of schematics showing a model of bacterial adhesion and cell cluster formation on narrow protruding line patterns. Bacteria approach PDMS surfaces modified with narrow topographic line patterns, FIG. 8(a1) and wide line patterns/smooth surfaces FIG. 8(b1). Bacterial attachment on top of narrow line patterns, FIG. 8(a2) and wide line patterns/smooth surfaces, FIG. 8(b2). Cell cluster formation on top of narrow line patterns, FIG. 8(a3), and wide line patterns/smooth surfaces, FIG. 8(b3).

Figure 9:
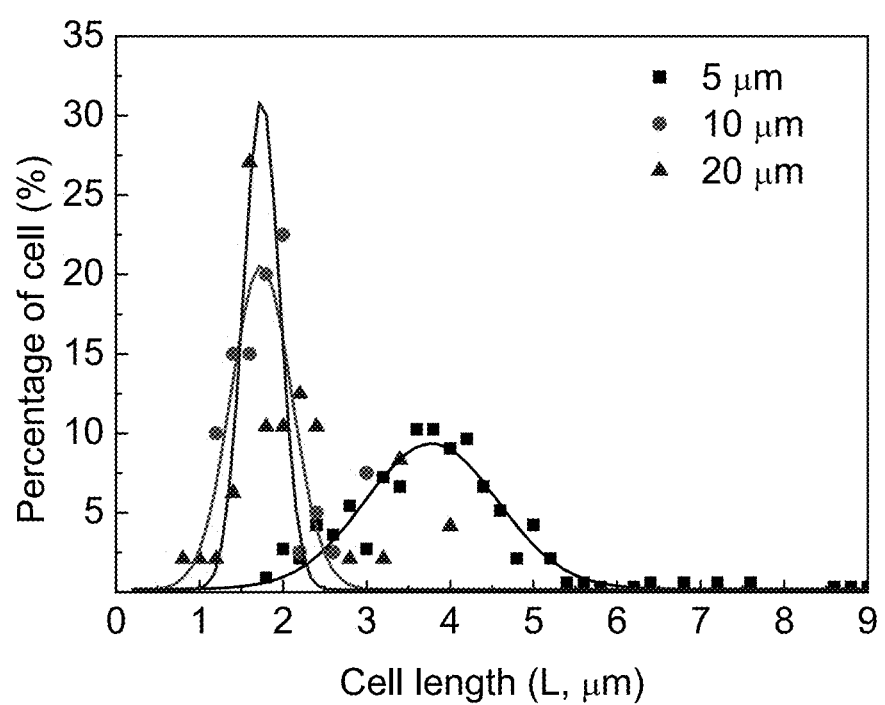

FIG. 9 is a graph showing cell length of attached WT E. coli cells on narrow (5 µm) line PDMS patterns after 2 h attachment or in 24 h biofilms, medium (10 µm), and wide (20 µm) line PDMS patterns.

Figures 10A, 10B, 10C:
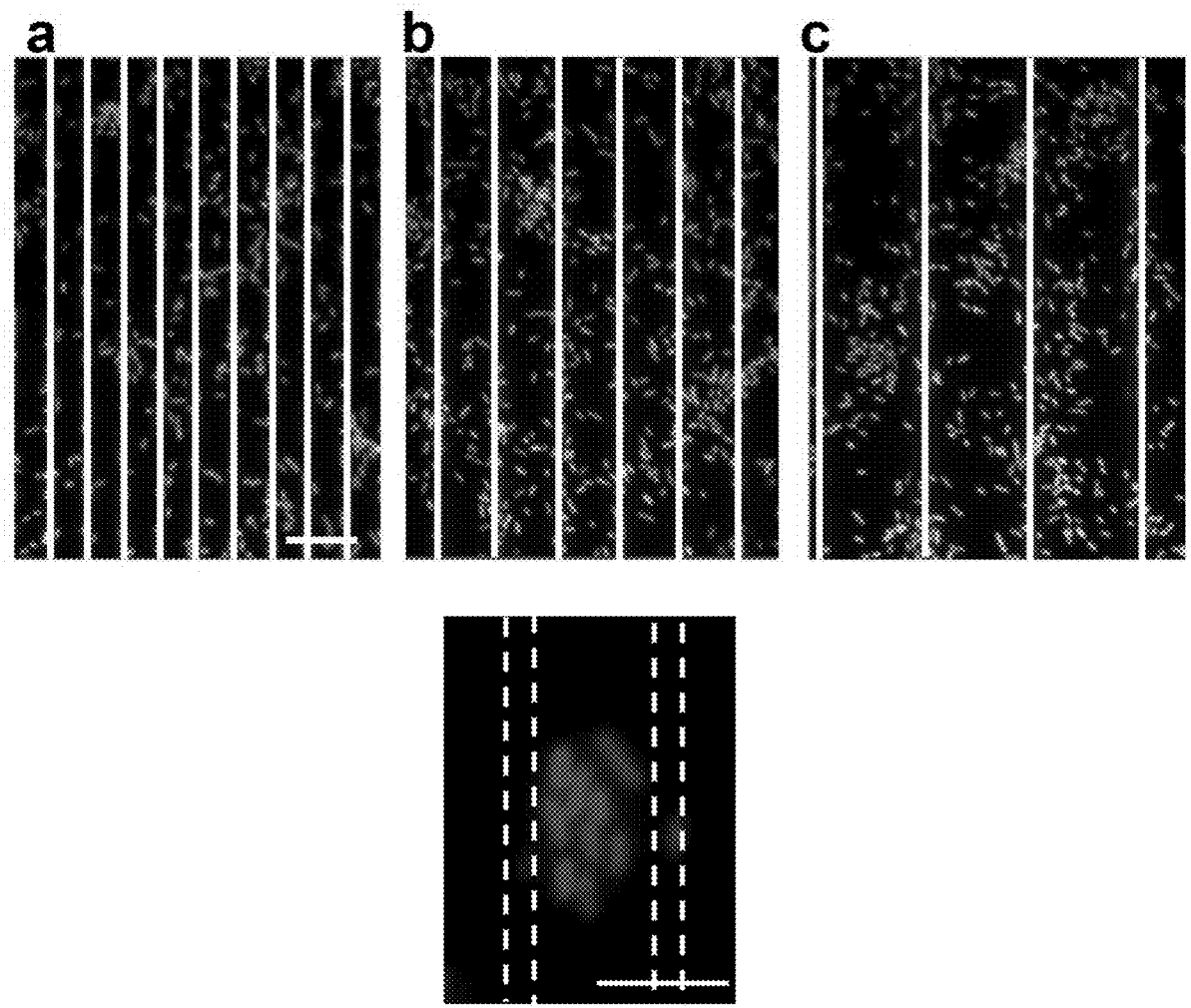

FIGS. 10(a) through 10(c) are representative fluorescence images of 24 h WT E. coli biofilm cells on line patterns with 3 µm inter-pattern distance. Cells were labeled with acridine orange. Edges of patterns are labeled with white lines.

Figure 11:
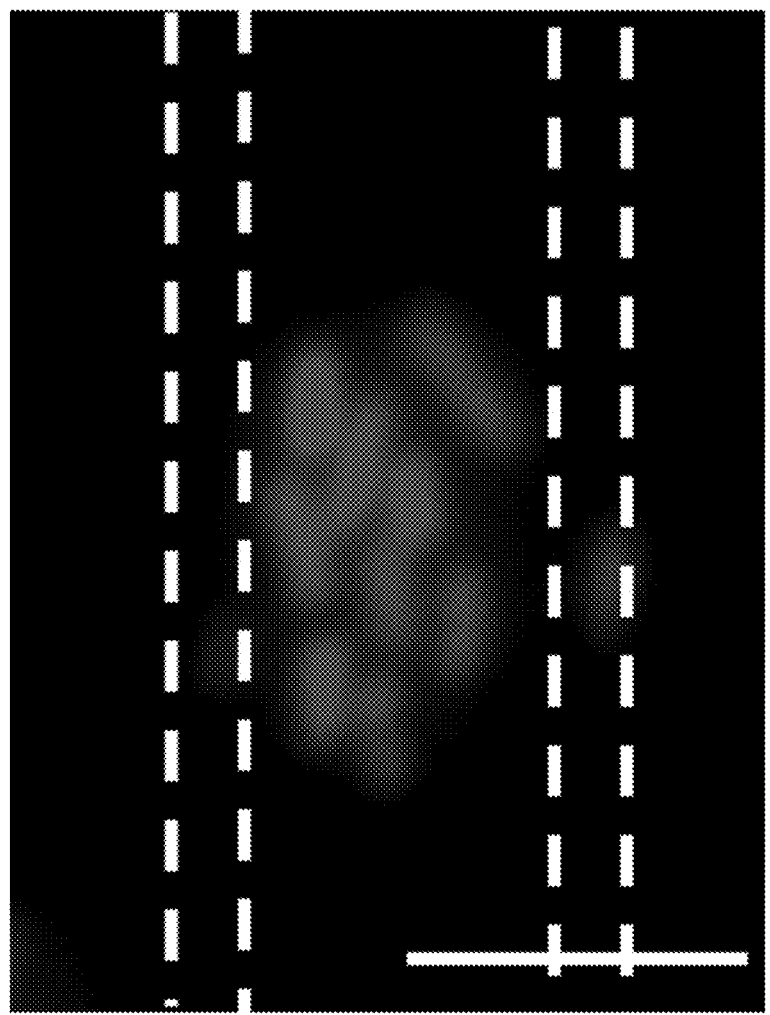

FIG. 11 is a representative fluorescence images of 24 h E. coli RH02/pRSH103 biofilm cells on line patterns with 3 µm inter-pattern distance. Edges of patterns are labeled with dotted white lines.

FIGS. 12(a) through 12(c) are graphs showing the distribution of cell orientations on top of 5 µm wide line patterns (mean±standard error). FIG. 12(a) is the complemented fimA mutant E. coli RH02/pRHG05. FIG. 12(b) is the complementedfliC mutant E. coli RH02/pRHG05.

FIGS. 13(a) through 13(c) are graphs showing the distribution of cell orientations on top of 5 µm wide line patterns (mean±standard error). FIG. 13(a) is wild-type P. aeruginosa strain PA14, FIG. 13(b) is ΔfliC mutant of PA14 (PA1092), and FIG. 13(c) is ΔpilB mutant of PA14 (PA4526).

FIGS. 14A(a) and 14(b) are a schematic illustrations of the catheter design with dynamic control of interior topography. FIG. 14(a) is side view of the catheter showing the spirial line patterns. FIG. 14(b) is a cross-section view of the catheter showing the distribution of nm and µm topographic line patterns. The height of mm scale lines will be ⅒ of the inner diameter of the catheter. The one with $D_i$ of 4.5 mm is shown as an example. The µm scale patterns will be selected based on biofilm test regardless of the catheter diameter.

Figure 15:
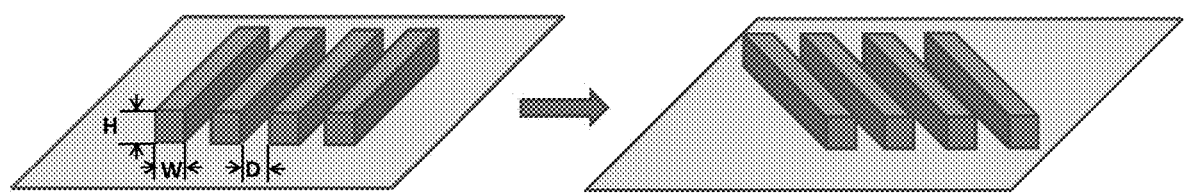

FIG. 15 is a schematic of the thermoresponsive change in the orientation of line patterns.

FIGS. 16(a) and (b) is a series of charts and images of biofilm formation of P. aeruginosa PAO1 on static flat control and programmed substrates (both flat substrates and substrates patterned with 10 µm deep recessive hexagonal patterns) fixed with a temporary but stable uniaxial strain of >50% so as to contract by ~50% when heated to 40° C. FIG. 16(a) shows the biomass and FIG. 16(b) are representative fluorescence images of P. aeruginosa PAO1 biofilms on different surfaces before and after trigger (10 min incubation at 40° C.) (Bar=50 µm). Mean±standard error shown.

FIG. 17(a) through (d) is a series of images and graphs of biofilm removal during shape change. FIG. 17(a) is a 3D image of P. aeruginosa PAO1 biofilm detachment. This 3D image was taken when the rapid biofilm detachment occurred in the first 4.3 s after topographic transition started. Due to the fast cell movement, trajectories of detached cells and cell clusters were recorded as the z stage moved upwards (representative cells highlighted using white arrows). FIG. 17(b) is a graph of the length and width of recessive hexagonal patterns measured during topographic change and the surface coverage of P. aeruginosa PAO1 biofilms at 0, 4.3, 360, and 600 s after the beginning of shape recovery and the final surface after washing. FIG. 17(c) and FIG. 17(d) are fluorescence images of P. aeruginosa PAO1 biofilms on topographically patterned programmed substrates, FIG. 17(c), and static flat control, FIG. 17(d), during triggered shape change (10 min incubation at 40° C.) (Bar=50 µm). Images show that cell clusters were removed from the patterned SMP with shape change but remained on the flat control surfaces.

FIGS. 18(a) and (b) are graphs showing that SMP is not toxic to P. aeruginosa PAO1 cells. FIG. 18(a) is a graph of the growth curves of P. aeruginosa PAO1 in the presence of different amounts of SMP (0, 1, 5, or 10% wt/vol). FIG. 18(b) is a graph of the effect of 10 min incubation at different temperatures (37, 38, 39, 40, 41, or 42° C.) on the viability of P. aeruginosa PAO1 cells. Mean±standard error shown.

DETAILED DESCRIPTION OF THE INVENTION

The present invention comprises the determination of the design characteristics for topographic patterns that will prevent bacterial adhesion and biofilm formation and the use of those patterns on the surfaces of certain devices that are prone to bacterial adhesion and biofilm formation. The technology can also be used to create smart medical devices that can remove biofilms on demand if they are formed over time.

Example 1

In light of the finding that the attachment of E. coli cells on 10 µm tall protruding square shaped PDMS patterns is significant only if the patterns are 20 µm×20 µm or bigger on face-up patterns and 40 µm×40 µm or bigger on face-down patterns, surface topography was believed to affect cell orientation and cell cluster formation during biofilm formation. In order to explore that conclusion, PDMS was used to create certain topographic patterns because it is a material commonly used in medical devices and possesses many features that make it desirable for biofilm study; e.g., it is nontoxic and suitable for creating µm scale patterns.

Results

Narrow Line Patterns Reduced E. coli Biofilm Formation on PDMS Surfaces

E. coli RP437/pRSH103 (henceforth WT E. coli) cells were cultured to study adhesion and biofilm formation on smooth PDMS surfaces and PDMS with 5 µm tall line patterns with varying width and distance between lines [Narrow (W=5 µm), Medium (W=10 µm), and Wide (W=20 µm); FIG. 1a]. To compare cell adhesion, the biomass of biofilms on modified PDMS surfaces and flat PDMS surfaces after 24 h incubation was quantified. The results showed that surface topography has profound effects on bacterial adhesion and subsequent biofilm formation. As shown in FIG. 1b&c, the biomass of biofilms on smooth PDMS surfaces was 0.78±0.09 µm³/µm², higher than that on surfaces with any line patterns tested in this study, e.g. 0.46±0.005 µm³/µm² on PDMS with 20 µm wide patterns and 20 µm inter-pattern distance. The total biomass of biofilms on PDMS surfaces modified with line patterns increased with pattern width. The inter-pattern distance did not affect biofilm formation on surfaces with wide patterns, but the total biomass increased with inter-pattern distance on surfaces with narrow patterns (5 µm wide). For example, the biomass on PDMS surfaces modified with 5 µm wide line patterns was 0.25±0.02 µm³/µm² and 0.38±0.02 µm³/µm² when the inter-pattern distance was 3 and 20 µm, respectively. Hence, 5 µm wide line patterns with 3 µm inter-pattern distance reduced biofilm formation by 62% compared to smooth PDMS surfaces. More reduction was observed for biofilm formation on top of line patterns, which was around 90% less than biofilms on smooth PDMS surfaces (FIG. 1d). The biomass of cells attached on top of line patterns increased with pattern width; however, inter-pattern distance did not show significant effect. For instance, the biomass was 0.12±0.004 $\mu m^3/\mu m^2$ and 0.36±0.06 $\mu m^3/\mu m^2$ on 5 and 20 μm wide patterns with 3 μm inter-pattern distance. Collectively, the data suggest that narrow patterns are less prone to biofilm formation.

Cell Cluster Formation is Hindered on Top of Narrow Line Patterns

Cell cluster formation is an important step towards the formation of mature biofilms. Cells in close proximity to each other can communicate through chemical and physical means, which play important roles in biofilm structural organization and associated drug resistance. Considering the significant role of cell cluster formation during biofilm formation, we were interested in studying if the reduction of surface coverage on narrow line patterns was due to the decrease in cell cluster formation.

To investigate the effects of surface topography on cell cluster formation, the distribution of cells attached on top of line patterns was characterized. A cluster was defined as a group of six or more cells all within 1 μm of a neighboring cell. This relatively stringent criterion allowed us to focus on the cells that have close interactions. The percentage of cells in clusters was calculated by dividing the number of cells in defined clusters with the total cell number on the surface of interest. The results revealed that pattern width is positively correlated with cell cluster formation on top of line patterns (p<0.001, ANOVA followed by Tukey test). For example, the percentage of cells associated with a cell cluster was 2.0±3.2%, 11.0±1.6%, and 22.3±1.8% on 5, 10, and 20 μm wide patterns when the inter-pattern distance was 3 μm (FIG. 1e). Cluster formation on the widest (20 μm) patterns tested with the largest inter-pattern distance (20 μm) was found to be 32.8±8%, close to that on flat PDMS, which was 30.0±0.03%. In comparison, inter-pattern distance showed similar effects on cluster formation compared with surface coverage. Therefore, patterns with the narrowest width (5 μm) and inter-pattern distance (3 μm) tested here reduced cluster formation to 2.0±3.2% (14 fold reduction compared to the flat PDMS). This significant reduction of cell cluster formation on narrow line patterns is consistent with the decrease of surface coverage.

Interestingly, the length distribution of attached cells varied with the pattern width. It was found that the cells on narrow line patterns (5 μm wide) were ~2 times longer than the cells on medium and wide line patterns both at 2 h (initial attachment) and 24 h (established biofilm) after inoculation (p<0.0001, ANOVA followed by Tukey test; FIG. 9). No significant difference was found between cells on medium and wide line patterns. This result suggests that surface topography can influence the physiology of attached bacterial cells, and certain topographic patterns may create stress conditions to the attached cells.

The size of bacterial cells is known to be influenced by their metabolic activities. Inspired by this, we compared the transcriptional activities of cells by labeling them with acridine orange which shows green and red fluorescence when binding to DNA and RNA of bacteria respectively. Representative images of fluorescently labeled WT *E. coli* cells on PDMS surfaces modified with line patterns were summarized in FIG. 10. After incubation for 24 h, cells on narrow line patterns showed stronger red fluorescence compared with cells on medium and wide line patterns, which indicates that the cells attached on narrow line patterns had more of RNA and thus higher level of overall gene expression.

Figures 2A, 2B, 2C, 2D:
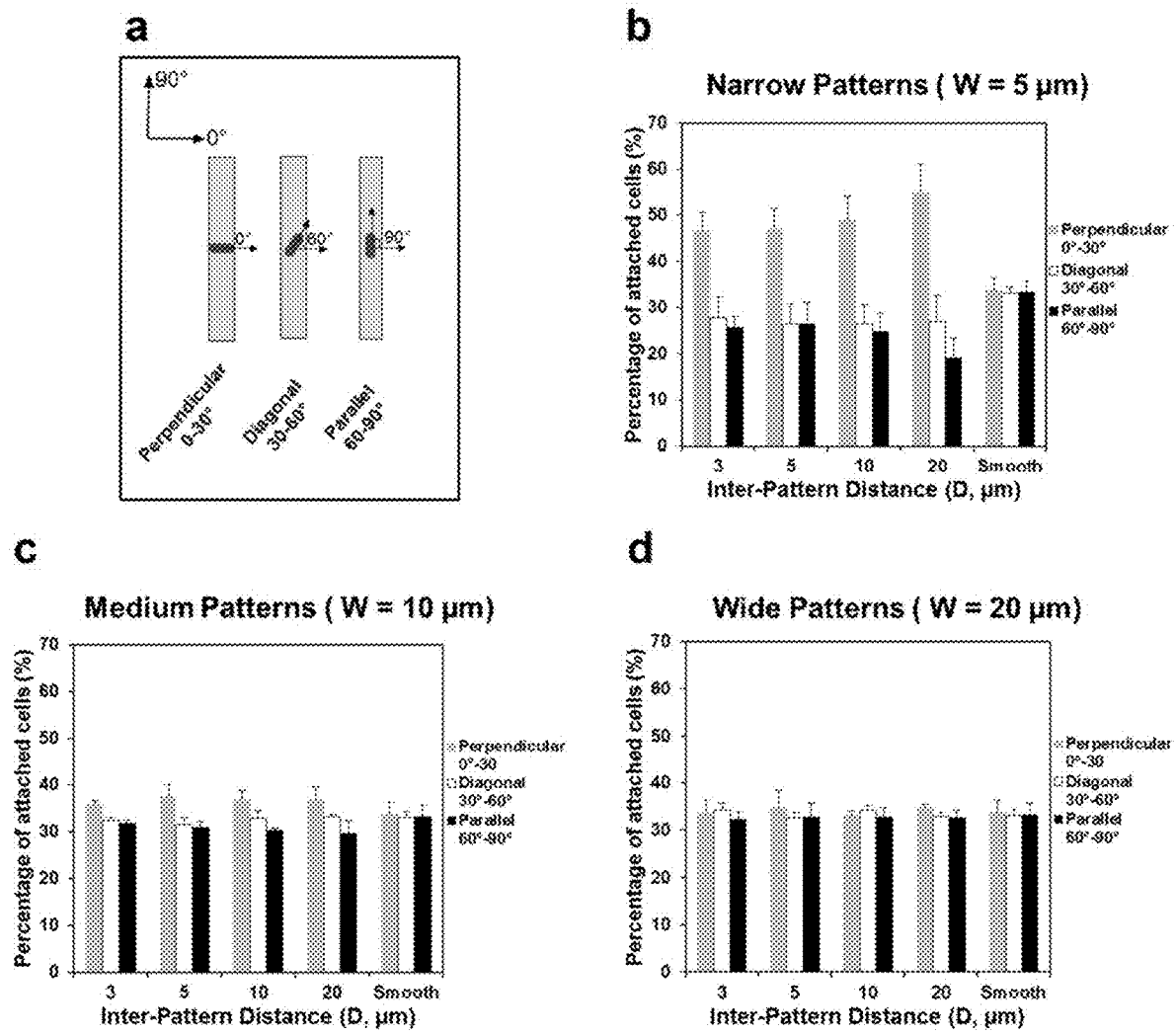

*E. coli* Cells Attached on Narrow Line Patterns Exhibited Preference in Cell Orientation In addition to the differences in surface coverage, cell cluster formation, and cellular activities, we also observed that pattern width affects the orientation of cells attached on top of protruding line patterns. Specifically, the orientation of WT *E. coli* cells attached on smooth PDMS surfaces and PDMS with 5 μm tall line patterns of different widths were compared. The inter-pattern distance was varied to be D=3, 5, 10, or 20 μm. At least 6 images were randomly collected and analyzed for each condition. Thus, over 5,000 WT *E. coli* cells on the line patterns were imaged and analyzed in total for their orientation [Perpendicular (0-30°), Diagonal (30-60°), or Parallel (60-90°) with respect to the orientation of the lines; FIG. 2(a)].

The results showed that the distribution of attachment angles was uniform on the PDMS surfaces without topographic modification (no bias in orientation of the attached cells, FIG. 2(b); p>0.05, ANOVA followed by Tukey test). In comparison, pattern width has an interesting and profound effect on cell orientation. Specifically, cell orientation on top of narrow line patterns (5 μm wide) was more skewed towards a perpendicular orientation with respect to the direction of the line patterns (0-30° on narrow patterns) (p<0.0001, ANOVA followed by Tukey test). As shown in FIG. 2(b), on patterns with 5 μm width and 3 μm inter-pattern distance, more cells (46.5±6.8% of the total cells) oriented between 0-30° (perpendicular to line patterns), followed by those between 30-60° (27.8±7.7%) and 60-90° (25.6±4.5%). On medium width patterns (W=10 μm), the cell orientation were found to be more uniformly distributed than on the narrow patterns, yet exhibited a slight, albeit consistent skew towards a perpendicular orientation (FIG. 2(c), p<0.0001, ANOVA followed by Tukey test). The wide patterns showed a near-uniform distribution of attachment angles (FIG. 2(d)) (p>0.05, ANOVA followed by Tukey test), which was also found on smooth surfaces (p>0.05, ANOVA followed by Tukey test). These results suggest that pattern width has a strong impact on the orientation of attached WT *E. coli* cells.

Preference in Cell Orientation Involves Cellular Activities

Both physical factors (Brownian motion, gravity, electrostatic interactions, hydrodynamics, or van der Waals forces) and bacterial activities (bacterial motility, production of exopolysaccharides, or usage of outer membrane structures) can affect the initial cell attachment to a surface during biofilm formation. To understand if the observed preference in cell orientation was simply due to physical factors during settlement or involved active response of bacterial cells to surface topography, the orientation of the WT *E. coli* cells on top of 5 μm wide line patterns after 2 h of initial attachment was also analyzed. The result showed that initially attached cells after 2 h of inoculation also preferred to land perpendicularly to the direction of 5 μm wide line patterns (FIG. 3, p<0.0001, ANOVA followed by Tukey test). In fact, the percentage of cells that aligned perpendicularly after 2 h of inoculation was even higher than that in 24 h biofilms. For example, 62.5% cells (compared to 46.5% cells in 24 h biofilms) attached perpendicularly to the line patterns with 3 μm inter-pattern distance (FIG. 3 & FIG. 2b). These results suggest that the perpendicular orientation is favorable for initial attachment and the cells may have adjusted orientation after initial attachment.

To understand if cellular activities are involved in the orientation of cell adhesion, the WT *E. coli* cells were pretreated with 10 μg/mL chloramphenicol (to inhibit protein synthesis) for 1 h before inoculation for attachment on top of 5 μm wide line patterns (FIG. 4). As shown in FIG. 4, the orientation of these pretreated WT *E. coli* cells after 24 h incubation was more skewed toward diagonal (30-60°) orientation rather than perpendicular (0-30°) orientation observed for untreated cells (FIG. 2b), possibly for the maximum contact for settlement of immobile cells. This result suggests that cellular activities were involved in the adjustment of cell orientation during attachment on 5 μm wide patterns.

Mutation of Key Genes Affected Cell Orientation on Line Patterns

To further understand what bacterial activities are involved in the preference of cell orientation, the orientation of four isogenic mutants of the WT *E. coli* [luxS (KX1485), motB (RP3087), fliC (RHG01), and fimA (RHG02)] on narrow line patterns were characterized. These mutants were selected because the corresponding genes are well documented to be important to bacterial adhesion and biofilm formation. The fliC gene encodes flagellin, which is the major component of flagella. Flagella are well known surface appendages that allow bacterial cells to move and make initial contact with a solid surface during biofilm formation by overcoming the long range repulsive force along the surface. Recently, Friedlander et al. reported that flagella are also used by *E. coli* cells to adhere to PDMS surfaces modified with an array of hexagonal features (2.7 μm in height and 3 μm in diameter) and overcome these unfavorable surface topographies by exploring the extra surface provided by the topography. The moB gene encodes a stator protein MotB, which plays an important role in the control of flagellar rotation. The fimA gene encodes the subunit of fimbriae, bacterial appendages involved in adhesion and movement on a solid surface. To understand if cell-cell signaling is important, the mutant of luxS gene was included, which is essential for the synthesis of quorum sensing signal AI-2.

Figure 12:
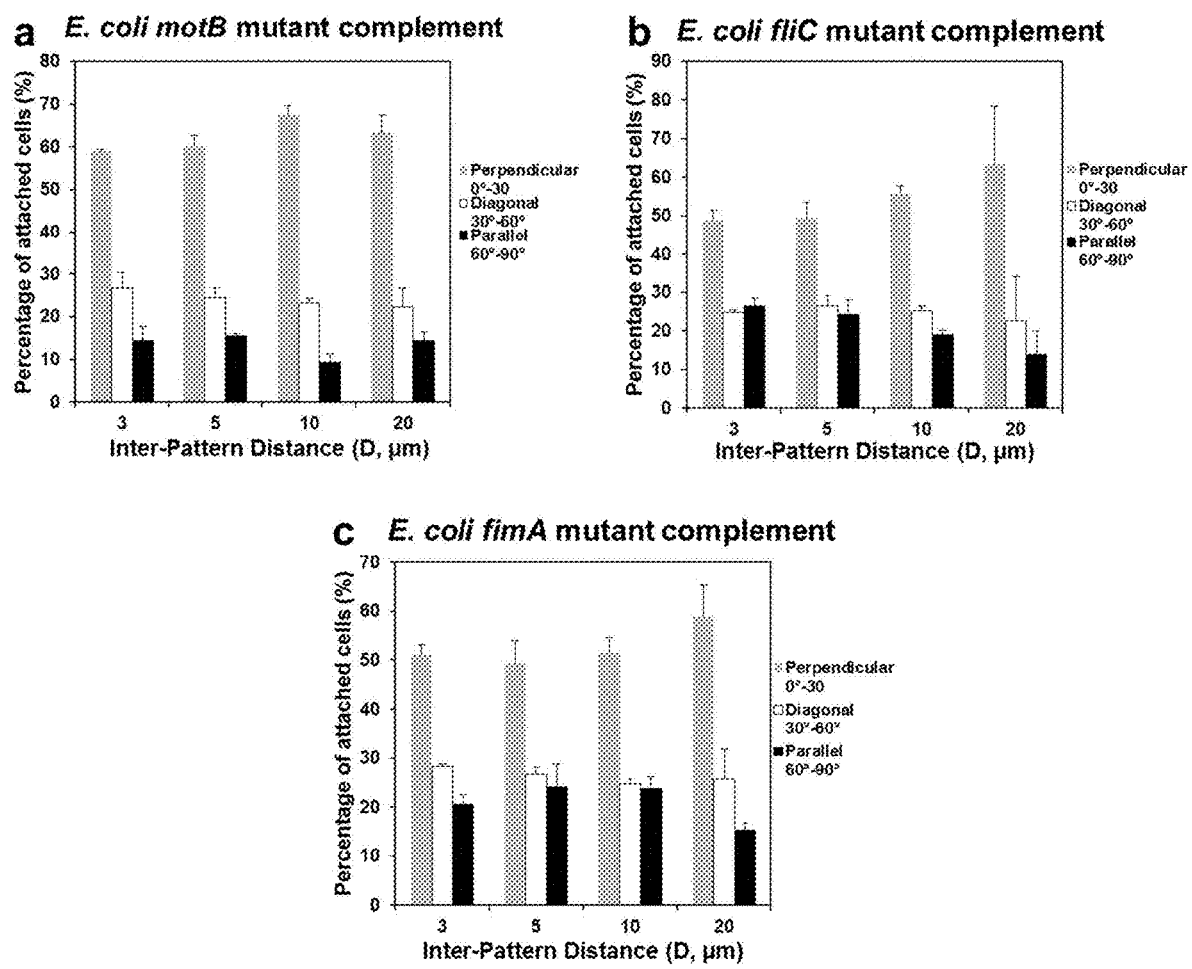

It was found that mutation of fliC, motB, or fimA abolished the preference in cell orientation exhibited by the wild-type strain, while the mutation of luxS gene did not show such effect. Especially, the fimA mutants preferred to align parallel to the orientation of line patterns in 24 h biofilms, which could be a result of the uniform cell orientation in cell clusters (FIG. 11). The fimA mutants failed to rearrange their orientation in cell cluster, which could be due to the different surface chemistry of the mutants compared with the WT *E. coli* cells because of the absence of fimbriae subunits on cell surface. To confirm that the results of motB, fliC, and fimA mutants were not due to any polar effects, the mutations were complemented with plasmids pRHG03, pRHG04, and pRHG05 carrying motB, fliC, and fimA genes respectively, all under the control of a lac promoter. As shown in FIG. 12, the defects of all three mutants were rescued by complementation.

Bacterial Flagella May be Involved in the Arrangement of Cell Orientation on Line Patterns To further investigate how bacteria actively chose the angle of attachment, cells were followed in real time after inoculation using fluorescence microscopy. It was found that some cells settled onto the top of 5 μm line patterns right after landing on the surface; while some cells contact the surface with one pole first and then settled perpendicularly on top of line patterns after spinning several rounds (FIG. 6). A series of time-lapse images of a representative attached cell are shown in FIG. 6. This observation is consistent with the phenomenon reported by Silverman et al. that *E. coli* W3110 cell body will spin if a single flagellar filament (hook or polyhook) is attached to the substratum, preference of orientation on top of narrow line patterns.

Figure 13:
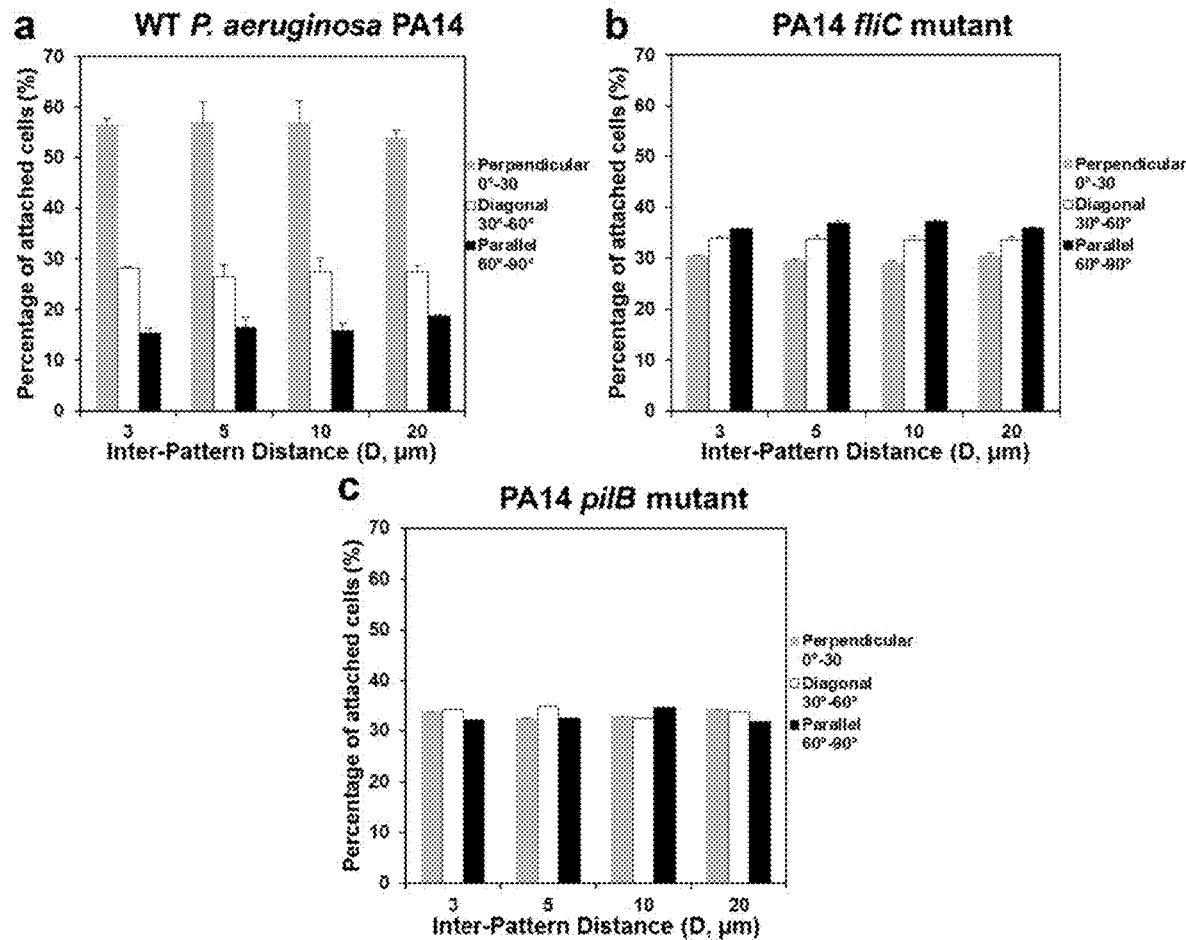

*E. coli* has both polar and lateral flagella. The rotation of *E. coli* cells during attachment (FIG. 6) suggests that the polar flagella play a key role in this process. To corroborate this result and understand if the lateral flagella are also important, we characterized the cell orientation of the wild-type *Pseudomonas aeruginosa* PA14 on top of 5 μm line patterns since *P. aeruginosa* cells only have a polar flagellum. As shown in FIG. 13, the percentage of attached PA14 cells that aligned perpendicularly on the 5 μm line patterns is even higher than the WT *E. coli* cells. For example, the percentage of attached cells that aligned perpendicularly was around 56.5% when the inter-pattern distance was 3 μm (compared to 46.6% for the WT *E. coli* cells). These results indicate that polar flagella play an important role in the control of cell orientation on PDMS surfaces. Consistent with the *E. coli* results, mutation of the fliC and fimA gene in *P. aeruginosa* PA14 also abolished the preference in cell orientation on narrow line patterns (FIG. 13), which supports our findings that flagella, especially polar flagella, and fimbriae played important roles in this phenomenon.

Biofilm Formation on PDMS Surfaces Modified with Hexagon Shaped Topographies

Based on the obtained results, hexagon shaped patterns were designed to further reduce biofilm formation (FIG. 7(a)). The hexagon shape was chosen to break up the cell-cell interaction between cells in the valleys between adjacent protruding features. We hypothesized that hexagon patterns with a size smaller than the critical dimension of 20 μm×20 μm and a narrow inter-pattern distance (3 μm) can effectively reduce biofilm formation. To test this hypothesis, 24 h biofilm formation of WT *E. coli* cells on PDMS surfaces embossed with hexagon shaped patterns with side length (L) of 2, 5, 10, or 20 μm and inter-pattern distance (D) of 2, 5, 10, 15, or 20 μm were tested (FIG. 7b). The total biofilm biomass on the modified PDMS surfaces was quantified. The results showed that hexagon shaped patterns with 15 μm side length and 2 μm inter-pattern distance was able to reduce total biofilm formation by 84% which is higher than the 62% percent reduction on PDMS surfaces with 5 μm wide line patterns and 3 μm inter-pattern distance (FIG. 7c). Collectively, by inhibiting cell-cell interaction between cells on top of topographies and in the valley between topographies, surface topography can efficiently reduce bacterial biofilm formation.

Discussion

As one of the promising strategies to prevent bacterial adhesion and subsequent steps of biofilm formation, the effects of surface topography on biofilm formation have been intensively studied recently. However, how surface topography affects bacterial physiology and how bacteria respond to topographic features are still unknown. To better understand the underlying mechanism, we systematically compared biofilm formation and bacterial adhesion on line patterns with varying width and inter-pattern distance in this study.

The narrow line patterns (5 μm wide) was found to reduce the surface coverage by up to 5-fold on top of the plateaus compared with the smooth PDMS surfaces. Consistently, such topography also reduced cell cluster formation by 14 fold. To investigate how surface topography influenced cell cluster formation, the orientation of attached cells were characterized and cells were found to land more perpendicularly to the direction of narrow patterns line patterns compared with the wide patterns and smooth PDMS surfaces. Both flagella and fimbriae mutants exhibited major defects in the pattern of cell orientation exhibited by the wild-type strain. Flagella are important for overcoming repulsive force along a solid surface to allow the initial contact of a bacterial cell with the surface. Besides, recent research has also shown that flagella play important role in overcoming unfavorable surface topographies during bacterial adhesion, and the interaction between cells and cell clusters. The real-time images of attachment and the finding that *P. aerugionsa* cells (only have polar flagella) have the same preference in cell orientation suggest that polar flagella are important to the observed preference in cell orientation.

Based on the results of this study, we proposed the following model to explain the preference of cell orientation on top of narrow patterns. As shown in FIG. 8a&b, when bacteria approach a solid surface, the cells make initial surface contact using flagella. On top of wide line patterns or smooth surfaces, the cells can land with a random angle of flagella-surface contact, leading to a uniform distribution of cell orientation. On narrow patterns; however, the angle of contact is important (FIG. 8a1). For a cell to attach on top of narrow protruding line pattern and orient in parallel to the line, the flagella need to hit the center of the line to allow sufficient cell-surface contact after landing. If the lines are narrow, such events are infrequent leading to a low percentage of cells aligned in parallel to the line patterns. After the initial attachment was made by flagella, bacterial can spin. If the flagellum is tethered to the side of a topographic feature, bacterial cell body will experience solid and liquid interface or no interface when it rotates (FIG. 8a2). With different interfaces, bacterial cell bodies will be challenged by different levels of stress. Thus, the mechanical signal transmitted into bacteria via flagellar stators may vary, which could contribute to the preference of initial attachment orientation on the surfaces with narrow line patterns. Following the settlement of bacterial cell body, bacterial fimbriae may be involved in further adjustment of cell orientation as evidenced by the defects in fimA mutant. Because the average length of WT *E. coli* cells on top of narrow PDMS line patterns in this study was 4±1.4 µm and the width of narrow PDMS surfaces was 5 µm, the head-to-toe interaction between bacterial cells can be efficiently interrupted (FIG. 8a3). This may partially contribute to the higher level of stress on narrow patterns (based on acridine orange staining) and the reduced cluster formation and biofilm mass. This is consistent with the results of this study and the our early finding that a threshold area (20 µm by 20 µm for face-up patterns and 40 µm by 40 µm for face-down patterns) is required for significant attachment of *E. coli* cells on protruding PDMS square patterns.

In summary, the effects of surface topography on the attachment, cluster formation and orientation of bacterial cells on top of protruding line patterns with varying width was investigated. The data revealed that both *E. coli* and *P. aeruginosa* cells prefer to align perpendicularly to the direction of narrow line patterns. As the line patterns got wider, the orientation of cells became more random; and cluster formation and cell density increased toward those on smooth PDMS surface. Both flagella and fimbriae were found important to the observed preference in cell orientation. These findings complement previous studies and provide new evidence that bacteria do "read the map" during biofilm formation. The data shed new light on the mechanistic understanding of biofilm formation and may help design better nonfouling surfaces.

Methods

Bacterial Strains and Growth Medium

*E. coli* RP437/pRSH103 is a motile and chemotaxis wild-type (WT) strain and referred as WT *E. coli* in this study. This strain and its four isogenic mutants (motB, luxS, fliC, and fimA) as seen in Table 1 below were used to investigate the orientation of attached cells on top of PDMS line patterns.

TABLE 1

| Strain | Genotype | Characteristics |
| --- | --- | --- |
| *E. coli* Strains | | |
| RP437 | Wild type [thr-1(Am) leuB6 his-4 metF159(Am) eda-50 rpsL1356 thi-1 ara-14 mtl-1 xyl-5 tonA31 tsx-78 lacY1 F⁻] | Wild type strain for biofilm study |
| RP3087 | RP437 (motB)580 | Motility mutant (point mutation in motB gene) |
| KX1485 | RP437 ΔluxS::Cm$^r$ | Quorum sensing mutant, unable to synthesize AI-2 |
| RHG01 | RP437 ΔfliC::Kan$^r$ | Unable to synthesize the subunit of flagella |
| RHG02 | RP437 ΔfimA::Kan$^r$ | Unable to synthesize the subunit of fimbriae |
| *P. aeruginosa* strains | | |
| PA14 | Wild type [Human clinical isolate; Rif$^r$] | Wild type strain for biofilm study |
| PA1092 | PA14 (fliC) | Flagellin type B transposon insertion mutant |
| PA4526 | PA14 (pilB) | Type 4 fimbrial biogenesis protein PilB transposon insertion mutant |

This WT *E. coli* was also used to study the formation of cell clusters on top of line PDMS patterns. *E. coli* RP437 was chosen because it is a model strain for biofilm research and allows us to compare with our previous results of this strain. The plasmid pRSH103 carries the dsRed gene, which labels the cells with constitutive red fluorescence. All *E. coli* cells were routinely grown at 37° C. with shaking at 200 rpm in Lysogeny Broth (LB) consisting of 10 g/L NaCl, 5 g/L yeast extract, and 10 g/L tryptone supplemented with tetracycline at a concentration of 30 µg/mL (henceforth LB-Tet).

A *P. aeruginosa* wild-type strain, PA14, and its two isogenic mutants (MC and pilB) were also used to study the orientation of attached cells on top of 5 µm wide PDMS line patterns. *P. aeruginosa* strains were grown at 37° C. with shaking at 200 rpm in LB.

4.2 Strain Construction

*E. coli* RP437 ΔfliC (*E. coli* RHG01) and RP437 ΔfimA (*E. coli* RHG02) were constructed using λ red recombination system. Briefly, the λ red recombination system on plasmid pKM208 was used to the replace target gene on the chromosome of *E. coli* RP437 with the polymer chain reaction (PCR) products containing kanamycin resistance marker flanked with ~700 bp of genomic sequence from each side of the target gene. The genomic DNA of JW4277 (ΔfimA::kan) and JW1908 (ΔfliC::kan) from the Keio collection were used as templates. Before the PCR products were electroporated into *E. coli* RP437 cells, the plasmid pKM208 was transformed into the *E. coli* RP437 cells. *E. coli* RP437/pKM208 cells were grown at 30° C. with 1 mM IPTG and 100 µg/mL ampicillin to promote the production of Red and Gam proteins. Gene deletion was verified by PCR using one primer upstream of the target gene and another primer within the drug marker. The plasmid pKM208 was cured after gene deletion by growing the mutants at 42° C.

Genetic Complementation of the Isogenic motB, fliC, and fimA Mutants

The isogenic mutants of motB, fliC, and fimA genes of the WT *E. coli* was complemented by cloning corresponding genes and their native ribosome binding site into the plasmid pRSH103. DNA fragments that contain the genes and their native ribosome binding site were amplified using primers with the chromosome DNA of WT *E. coli* as template.

The PCR products were inserted into the vector pRSH103 between the double sites (HindIII and SpeI) for genes fimA and motB or single restriction site (HindIII) for gene fliC. Isopropyl β-D-1-thiogalactopyranoside (IPTG) was added at 1 mM into the culture to induce the gene (controlled by a lac promoter).

Preparation of Surfaces with Topographic Patterns

Microfabrication of PDMS surfaces was achieved through photolithography and soft lithography by following previously described procedures with slight modifications. For all line shaped PDMS surfaces, pattern length (L) was fixed at 4 mm and pattern height (H) was fixed at 5 µm. The line patterns were designed to have width (W) of 5, 10, or 20 µm, and inter-pattern distance (D) of 3, 5, 10, or 20 µm (FIG. 1*a*). For all the hexagon shaped PDMS surfaces, pattern height (H) was fixed at 10 µm. The hexagon patterns were designed to have side lengths (L) of 2, 5, 10, 15, and 20 µm and inter-pattern distance (D) of 3, 5, 10, or 20 µm (FIG. 7*a*). The topographic features were created by using photolithography to etch silicon wafers with complementary patterns at the Cornell NanoScale Science & Technology Facility (Cornell University, Ithaca, N.Y., USA). Soft lithography was used to prepare the topographic PDMS patterns. Briefly, PDMS elastomer base and curing agent from SYLGARD184 Silicone Elastomer Kit (Thermo Fisher Scientific, Waltham, Mich., USA) were mixed at a 10:1 ratio (approximately 15 g of PDMS per set of patterns) and degassed for 30 minutes. The solution was poured slowly onto the silicon wafer and left to cure for 24 h at 50° C., followed by another 24 h to settle at room temperature. The PDMS patterns were then carefully peeled off the silicon wafers and individually cut and stored in petri dishes for later use in experiments.

Biofilm Formation

To study the orientation of attached cells and formation of cell clusters in biofilms formed on top of PDMS line patterns, overnight cultures of the WT *E. coli* and its four isogenic mutants were used to inoculate biofilm cultures (20 mL each of LB medium supplemented with 30 µg/mL tetracycline) in petri dishes containing sterilized PDMS surfaces to an initial optical density at 600 nm ($OD_{600}$) of 0.05. Biofilm cultures of PA14 and its two isogenic mutants were prepared in the same way in LB medium. Patterned PDMS surfaces were sterilized by soaking in 190 proof ethanol for 30 min and then dried in a clean petri dish for 40 min at 50° C. before inoculation. Biofilm cultures were incubated at 37° C. for 2 or 24 h without shaking. Bacterial attachment on top of 5 µm wide line patterns in static solutions was followed using a fluorescence microscope (Axio Imager M1, Carl Zeiss Inc., Berlin, Germany). Pictures and real time movies (for the WT *E. coli* on 5 µm wide line patterns) were recorded.

To study the settlement of the WT *E. coli* cells on top of line patterns, cells from an overnight culture were pretreated with 10 µg/mL chloramphenicol (Sigma Aldrich, St. Louis, Mo., USA) for 1 h at 37° C. with shaking at 200 rpm and then used to inoculate biofilm cultures as described above.

Microscopy

The PDMS surfaces with biofilms were gently washed three times with 0.85% wt/vol NaCl solution to remove planktonic cells. *E. coli* biofilms were imaged immediately after washing. *P. aeruginosa* biofilms were further labeled with acridine orange (Sigma Aldrich, St. Louis, Mo., USA) before imaging. To do this, the PDMS surfaces with *P. aeruginosa* biofilms were soaked in 3 mL acridine orange solution (0.5 mg/mL acridine orange in water with 5% vol/vol acetic acid to adjust pH to 3) for 5 min and gently washed three times in 0.85% NaCl solution to remove excessive dye. To study the cellular activity of WT *E. coli* biofilm cells on PDMS surface modified with line patterns, 24 h WT *E. coli* biofilms were also further labeled with acridine orange as described. All biofilms were visualized using an Axio Imager M1 fluorescence microscope (Carl Zeiss Inc., Berlin, Germany). At least five positions on each pattern were randomly selected for imaging. Each condition was tested with three replicates.

Image Analysis

Images were further analyzed using Adobe Photoshop CS5.1 to determine the orientation and clustering of bacterial cells attached on the line patterns. The orientation of each attached cell was measured by comparing to the orientation of the line pattern it is attached to. The axis perpendicular to the orientation of line patterns (horizontal in the FIG. 2*a*) was defined as 0°. Thus, the data of cell orientation were categorized as Perpendicular (0-30°), Diagonal (30-) 60°, or Parallel)(60-90° (FIG. 2(*a*)).

Statistical Analysis

One-way and Two-way ANOVA analyses were applied to understand the effects of surface patterns on orientation of attached cells and formation of cell clusters. All statistical analyses were performed by using SAS 9.1.3, Windows version (SAS, Cary, N.C., USA). Results with $p<0.05$ were considered statistically significant.

Example 2

Figure 14:
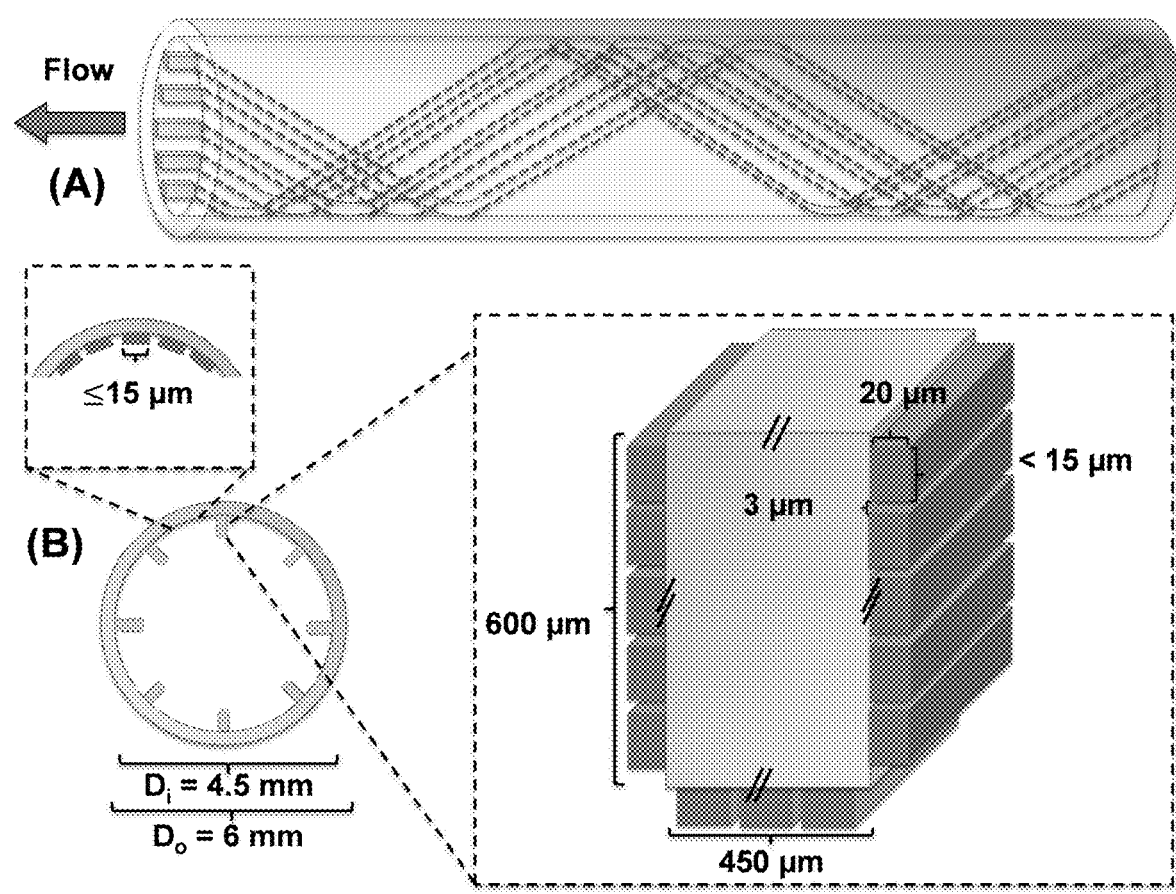

Based on the aforementioned design principles, catheters may include surface topographies that are simple to manufacture and effective to reduce bacterial adhesion without using antimicrobials. As shown in FIG. 14, the catheter may have 8 protruding lines with the height of 10% of the inner diameter of the catheter. On top of these lines and the rest of interior surface, we will introduce 20 µm tall line patterns with optimal width and inter-pattern distance (to be determined in this project). All line patterns will be in parallel with each other and be made to create waving patterns with the period of 10 times of $D_i$ (e.g. 4.5 cm for the catheter with a $D_i$ of 4.5 mm; FIG. 14(*b*)). The 20 μm tall line patterns can reduce fouling by decreasing bacterial attachment; while the 1/10 $D_i$ tall lines can change the pattern of bulk flow and increase the shear to further reduce bacterial adhesion and promote biofilm detachment.

Another level of biofouling control is afforded by the dynamic change of surface topography. The first generation of catheters may be made with a shape memory polymer that can maintain the original topography at 37° C., but switches to a different topography with a 60 degree change in the orientation of the line patterns upon triggered shape change, which can be achieved by different means including heating, electric control, magnetic field, laser, among others, as seen in FIG. 15. Such change in the orientation of line patterns will further detach bacterial cells, which will be removed by the flow of urine (the urine flow is turbulent with Reynolds number around 21,000 based on a recent study, which will further enhanced with our mm tall interior lines). The mm and μm patterns can be introduced during extrusion, added after the tube is made by molding, or made along with the rest of the catheter together using 3D printing. In addition to fouling control, the use of shape memory material also brings the possibility to reduce the diameter catheter before insertion and deploy the balloon structure without injecting water, which can reduce the manufacturing cost and ease the insertion process. We envision that in the second generation, the catheters will be made with triple shape memory polymers to allow the easy insertion with a thin tube, which will change to the final shape with patterns and balloon structure at body temperature rapidly upon insertion, undergoes a dynamic change of surface topography as described above during usage, and eventually triggered to convert to the final shape with a smaller diameter and deflated balloon for simple removal. Gentle heating above the body temperature for to trigger shape change can be achieved by infilling warm sterile water in the interior of the catheter and withdrawing after the shape change. If a temperature of 50° C. or higher is needed, heating can be achieved in a pulsating manner by repeating the process of infilling and withdrawing. This will ensure the rapid shape change without causing damage to human tissue. The liquid for heating can also be tailored to facilitate the killing and removal of biofilm cells (e.g., by changing pH or adding active ingredients).

To obtain shape memory, a system based on poly(ε-caprolactone)-oligo[3-(R)-isobutylmorpholine-2,5-dione] (PCL-PIBMD25) may be used as polyurethane is biocompatible, commonly used in catheters, and has excellent shape memory properties. The modulus of PCL-PIBMD25 is around 200 MPa at 37° C., which is excellent for the catheter applications. PCL-PIBMD25 may be synthesized by following the procedure described previously in three steps. The physical properties of PCL-PIBMD25 are listed in Table 4 below:

TABLE 4

The physical properties of PCL-PIBMD25.

| $T_m$ | $T_g$ | E when $T < T_{trans}$ | E when $T > T_{trans}$ |
|---|---|---|---|
| 170° C. | 43° C. | 202 ± 14 MPa | 0.61 ± 0.19 MPa |

To create topographic patterns, PCL-PIBMD25 may be heated to 180° C. ($T_m$=170° C.) and molded with a silicon wafer with complementary geometry of desired μm scale line patterns. After the system is cooled to room temperature, the polymer with line patterns may be peeled off to obtain the final shape. Then the polymer will be heated to 80° C. (above its $T_g$) and pressed against the same mold but with the orientation changed by 60° from the final pattern (left in FIG. 15). The system will then be cooled to room temperature to fix the temporary shape (secondary pattern; right in FIG. 15).

After the creation of topographic patterns we will test the shape change by first incubating the surface in Artificial Urine Medium (Cat. #102465-414, VWR) for 1 h at 37° C. The surface topography will be examined using light microscopy in DIC (differential interference contrast) mode. Then the temperature will be increased to its $T_g$ 43° C. and the shape recovery over time will be recorded. The surface will be kept in a petri dish with transparent bottom (Cat. #08-772-1, Fisher) and flow of heated medium to allow real time imaging at the desired temperature. The same test will be repeated with shape change temperature varied as 46, 48, 50, 52, 54, 56, 58, or 60° C. to identify the lowest temperature allowing rapid shape change. To allow effective biofilm detachment, the lowest temperature that allow more than 90% shape recovery within 5 min is preferred (occurs in 30 s when the polymer is heated to 60° C. according to literature).

PCL-PIBMD25 was chosen for the aforementioned reasons. The temperature of shape change is above body temperature. However, because the heating is temporary, it is not expected to cause any significant damage to host tissue. If necessary, the heating can be achieved by filling part of the catheter with warm sterile water. This can allow the heating to be centered for the interior of the catheter and stopped quickly by withdrawing the water. In case we meet any unexpected technical issues, we will consider alternative polyurethane based shape memory materials such as poly(tetramethylene glycol)-polyurethane, poly(ε-caprolactone)-polyurethane, poly(ethylene glycol)-POSS-PDI, MDI-PCL-BD, and poly(lactic acid)-polyurethane. These materials can be either purchased or readily synthesized by following reported protocols.

Due to the unique characters of urinary catheters, the new design should have the following features: (1) resistance to bacterial adhesion, (2) low manufacture cost, (3) ease of insertion and removal; (4) comfort of the patients during the indwelling time. Given these considerations, PCL-PIBMD25 may be used with topographic line patterns both at mm scale to increase flow shear and at μm scale to reduce fouling. The height of line patterns (H) will be at least 10 μm, while the width of patterns (W) and inter-pattern distance (D) will be systematically varied as 2, 5, 10, 15, and 20 μm. To ensure the throughput, patterns may be tested on flat surfaces to identify the optimal dimension first. The topographic patterns will be created using lithography at the Center of NanoFacilities at Cornell University as we described previously.

Bacterial adhesion may be tested on different patterns. The bacteria may be inoculated as $10^5$ cells/mL in the Artificial Urine Medium and incubated without shaking to compare bacterial adhesion and biofilm formation. To form biofilms, the above materials may be cut into 1 inch by 1 inch square coupons to culture biofilms in Artificial Urine Medium at 37° C. with no flow. Bacterial attachment will be followed by quantifying colony forming units (CFU) and 3D fluorescence imaging using Live/Dead staining. The amount of biomass and surface coverage will be quantified using the COMSTAT software. A clinical isolate of *E. coli* from ATCC (Table 2) may be used in this test. We believe that different dimensions will exhibit different levels of bacterial adhesion and biofilm formation; and thus, the best topographic pattern will be identified after comparing the aforementioned patterns. We expect that the presence of twisted mm tall line patterns to enhance flow shear will further reduce biofouling in the actual catheter.

A few patterns have been tested using PDMS and LB medium. The results showed that the PDMS surfaces with 5 μm tall, 5 μm wide patterns and 3 μm inter-pattern distance reduced 62% of 24-h biofilm formation on PDMS compared to the flat surface in the absence of flow (a rigorous condition to test anti-fouling properties). Thus, a pattern design has been found that is better than the regular flat surface.

Besides the effects on bacterial attachment afforded by surface topography, dynamic changes in surface topographic features can have more profound impacts on bacterial cells.

Using the optimal topography above, the effects of triggered shape change on biofilm detachment and the viability of biofilm cells can be tested. Because the patterns are at mm and μm scales, major killing effects on biofilm cells are not expected by triggering the change of surface topography except for the cells that are attached between protruding patterns. A rapid change of surface topography should disrupt the biofilm matrix and dislodge the attached cells and biofilms, leading to biofilm removal by urine flow and allowing extended duration of indwelling catheters.

Bacteria may attach on the patterns with the orientation shown in the left image of FIG. 15. The cells may be inoculated at a density of $10^5$ cells/mL in Artificial Urine Medium and incubated in the same medium at 37° C. for 24 h. Then the surface may be heated to 43° C. to trigger the shape change (same time of duration as determined above). The changes in the line patterns and associated changes in biofilm morphology/detachment may be followed in real time using a microscope with DIC lens. The amount of bacterial cells attached on the surface before and after shape change may be determined by counting CFU after removing the attached cells by gentle sonication as described previously. The CFU results may be corroborated with florescence microscopy using Live/Dead staining and the COMSTAT software as described above.

In addition to the *E. coli* strain described above, the present invention may be validated using several other bacterial strains that are known to cause CAUTIs as seen in Table 5 below. These strains are all clinical isolates from patients with UTI and are available from ATCC.

TABLE 5

Microbial species to be tested

| Species | ATCC strain number |
| --- | --- |
| Escherichia coli | 53505 |
| Candida albicans | 14053 |
| Enterococcus faecalis | 19433 |
| Klebsiella pneumoniae | 13883 |
| Pseudomonas aeruginosa | 27853 |
| Enterobacter cloacae | 13047 |
| Staphylococcus saprophyticus | 15305 |

Example 3

The present invention was evaluated in connection with the use of hexagonal patterns. Hexagonal patterns were used because the static protruding or recessive hexagonal patterns have been found to significantly reduce biofilm formation. Thus, they are good candidates for biofouling control using dynamic topography in this study. Another advantage to recessive hexagonal patterns is that they can maintain structural integrity under a uniaxial strain of >50%, an important step in creating the temporary shape. *Pseudomonas aeruginosa*, *Staphylococcus aureus*, and *Escherichia coli* were used as model species in this study due to their significant roles in biofilm infections.

In a proof-of-concept study, we chose an SMP based on t-butyl acrylate (tBA), poly (ethylene glycol)$_n$ dimethacrylate (PEGDMA), and photoinitiator 2,2-dimethoxy-2-phenylacetophenone (DMPA), which has one way shape memory around its glass transition temperature ($T_g$). The biocompatibility of this SMP has been validated by its cardiovascular applications. Stretched SMP surfaces used in this study were found to stably maintain their fixed temporary shape during 48 h incubation at room temperature in sterile LB medium. After 10 min incubation at 40° C., the programmed SMP shank with a 98.9% recovery to the permanent shape.

Static flat control (prepared without shape memory fixing so as not to change shape when heated to 40° C.) and both flat and topographically patterned programmed surfaces (fixed with a temporary but stable uniaxial strain of >50% so as to contract by ~50% when heated to 40° C.) were prepared. All surfaces were challenged with biofilm formation of *P. aeruginosa* PAO1, *S. aureus* ALC2085, and uropathogenic *E. coli* ATCC53505 for 48 h at room temperature.

The effects of static topography on adhesion and biofilm formation was studied by comparing the biomass of 48 h biofilms formed on these three different surfaces. For calculating biomass, 3D information was obtained from a series of z stack biofilm images (1 μm interval), which were then analyzed using the software COMSTAT. By analyzing the biomass of 48 h biofilms on these three different surfaces, hexagonal recessive patterns were found to significantly reduce microbial biofilm formation. For example, the biomass of *P. aeruginosa* PAO1 biofilms on topographically patterned programmed substrates (before triggered shape recovery) was 50.9±7.2% and 51.9±7.3% of that on flat programmed substrates and static flat control, respectively ($p<0.001$ for both, one way ANOVA adjusted by Tukey test) as seen in FIG. 16. No significant difference was found between static flat controls and flat programmed substrates (both around 9 μm$^3$/μm$^2$; p=0.93 one way ANOVA).

After 48 h of incubation, the effects of topographic changes on established biofilms were tested. Upon heating for 10 min at 40° C., shape recovery induced significant detachment of established biofilms. For example, the biomass on topographically patterned programmed substrates was 4.7±0.7 μm$^3$/μm$^2$ and 0.01±0.01 μm$^3$/μm$^2$ before and after shape recovery induced changes in surface topography, respectively. This represents a 469-fold reduction of biomass due to the change in substrate topography, and 909-fold reduction comparing to the 48 h biofilm biomass (9.1±0.8 μm$^3$/μm$^2$) on static flat controls without topographic patterns and shape change. Collectively, these data demonstrate up to 99.9% biofilm reduction through combined effects of biofilm inhibition by surface topography and biofilm removal by shape change. Similar effects of biofilm removal were also observed for flat programmed substrates e.g., the biomass on flat programmed substrates was 9.3±2.9 μm$^3$/μm$^2$ and 0.04±0.03 μm$^3$/μm$^2$ before and after shape recovery, respectively (231-fold reduction, p<0.001, one way ANOVA adjusted by Tukey test) as seen in FIG. 16(a). These results were corroborated by fluorescence images, as seen in FIG. 16(b), and colony forming unit (CFU) assay.

In contrast to the reduction in biomass observed on programmed substrates, the biomass on static flat controls before and after incubation at 40° C. for 10 min was 9.1±0.8 $\mu m^3/\mu m^2$ and 8.5±1.9 $\mu m^3/\mu m^2$, respectively (p=0.63, one way ANOVA), as seen in FIG. 16(a). Thus, the aforementioned biofilm removal was indeed caused by shape change rather than temperature change.

Biofilm dispersion was further verified by taking real-time movies. Before triggered shape change by heating for 10 min at 40° C., P. aeruginosa PAO1 biofilms were clearly seen with large cell clusters. When the shape recovery started, rapid detachment of both cell clusters and individual cells were observed on both topographically and flat patterned programmed substrates. Most changes in shape occurred in the first 6 min after shape recovery started as seen in FIGS. 17(a) and (b). Surface coverage by biofilms was 33.0% before shape recovery (t=0 s) and dropped to 19.9% after just 4.3 s of shape recovery as seen in FIG. 17(b). At 6 min, surface coverage further decreased to 11.1% as seen in FIG. 17(b). It is worth noticing that this experiment was conducted without flow, and a gentle wash after shape change was sufficient to remove nearly all detached cells as seen in FIGS. 16 and 17(c). Such detachment was not observed for the static flat control (no shape recovery), which was also incubated at 40° C. for 10 min as seen in FIG. 17(d). After 10 min shape recovery, the same cell clusters remained on these static control surfaces as seen in FIG. 17(d).

The biocompatibility of this SMP chemistry has been demonstrated by its cardiovascular application; however, the toxicity of the SMP to bacterial cells has not been evaluated. To test if this SMP is toxic to bacterial cells, planktonic P. aeruginosa PAO1 cells were grown in the presence of 0, 1, 5, and 10% (wt/vol) of the SMP. The planktonic growth of P. aeruginosa PAO1 in the presence of SMP was not significantly different than that of cells in LB medium (p>0.05, one way ANOVA), indicating that the SMP used this study is not toxic to P. aeruginosa PAO1 as seen in FIG. 18(a).

The effects of temperature change (10 min at 40° C.) on the viability of P. aeruginosa PAO1 were evaluated. By quantifying the number of viable cells after 10 min incubation at temperatures ranging from 37 to 42° C., the viability of P. aeruginosa PAO1 cells was not affected by any of the tested conditions as seen in FIG. 18(b)(p>0.05, one way ANOVA). These and the above results confirmed that the reduction in biofilm biomass was due to biofilm dispersion by shape recovery rather than the toxicity of SMP or thermo-induced killing.

To understand if the effects of dynamic topography are species specific, biofilm experiments were repeated using S. aureus and an uropathogenic E. coli strain. Similar to the results of P. aeruginosa PAO1, topographically patterned programmed substrates exhibited 39.8±4.0% inhibition of 48 h E. coli biofilm formation compared to the static flat control (p<0.001, two way ANOVA adjusted by Tukey test) before triggered shape change. No significant difference (both around 3.3 $\mu m^3/\mu m^2$; p=0.73, one way ANOVA) was found between static flat control and flat programmed substrates. The biomass of 48 h S. aureus biofilms on topographically patterned programmed substrates was similar to that on static flat control and flat programmed substrates (both around 5.5 $\mu m^3/\mu m^2$; p=0.22, one way ANOVA). Nevertheless, change in surface topography triggered by shape recovery still caused dramatic detachment of both E. coli and S. aureus biofilms. For example, the biomass of S. aureus biofilms on topographically patterned programmed substrates was 5.5±0.2 $\mu m^3/\mu m^2$ and 0.04±0.02 $\mu m^3/\mu m^2$ before and after shape recovery, respectively. Similar effects of biofilm removal were also observed for flat programmed substrates. In contrast, incubation at 40° C. for 10 min alone did not show significant effect on the biofilms formed on flat control substrates, showing that biofilm removal from stretched samples was indeed caused by shape recovery.

To understand the long-term effects of biofilm removal and how fast the remaining cells can reform biofilms, we followed the regrowth of P. aeruginosa PAO1 and E. coli ATCC53505 biofilms at 12, 24, and 48 h after shape recovery trigged biofilm removal, and compared the results with the biomass before shape recovery and the static flat control that underwent the same temperature change but not shape recovery. For both species, the biomass on the surfaces that had gone through shape recovery was significantly lower than that before shape recovery and on the static flat control. For example, the biomass of P. aeruginosa PAO1 biofilms on flat program surfaces was 1.6±0.1 $\mu m^3/\mu m^2$ at 48 h after shape recovery. This is 83.7% (p=0.0164, one way ANOVA adjusted by Tukey test) lower than that before shape change (9.3±2.9 $\mu m^3/\mu m^2$) and 89.0% (p=0.0022, one way ANOVA adjusted by Tukey test) lower than that on the static flat control (increased from 9.1±0.8 $\mu m^3/\mu m^2$ to 14.7±0.9 $\mu m^3/\mu m^2$ during the same period of incubation time). Even stronger effects were found for patterned programmed surfaces (additional 58.1% reduction than the above flat programmed surfaces; p=0.0002, one way ANOVA adjusted by Tukey test) and consistent results were obtained for E. coli ATCC53505 biofilms. Collectively, these results indicate that the biofilm regrowth after shape changes was relatively slow (83.7% and 85.8% less biofilm after 48 h regrowth compared the biomass after 48 h of the initial biofilm formation on new flat and patterned programmed surfaces, respectively), presumably because of the mass reduction of biofilm biomass by shape recovery Despite the extensive research on fouling control during the past decades, biocompatible materials that offer long-term biofilm control in complex environment are still yet to be developed. Moreover, removing mature biofilms that have large cell clusters and thick extracellular matrices remains as an unmet challenge. In this study, we introduced recessive hexagonal patterns on SMP substrates to inhibit biofilm formation and obtained dynamic change in surface topography upon triggered shape memory recovery. The shape-change-induced biofilm dispersion was fast (~6 mins) and can remove large clusters from mature biofilms. This material is also biocompatible, and the shape change can be triggered by gentle heating, without using an electric or magnetic field as required by some other systems.

The topography was created using soft lithography; thus, it is well defined and can be applied to a large surface area. Despite these advantages, we are aware that this SMP only has one way shape change. To be broadly adapted for diverse applications, the capability to go through cyclic changes in shape is desirable. Some shape memory polymer chemistries have been demonstrated to have two way, triple shape, or other forms of multi shape. In the future, we plan to test such polymers to obtain more sustainable antifouling properties. It will also be helpful for biomedical applications to have the temporary shape maintained at body temperature rather than room temperature. This is part of our ongoing study. With regards to the mechanism of biofilm dispersion, data presented herein revealed that biofilm dispersion was rapid and cell clusters were disrupted. The exact mechanism of shape memory recovery triggered biofilm removal is unknown. We speculate that the observed effects might be caused by disruption of biofilm matrix and cell-surface interactions. This is part of our ongoing work.

In summary, the present invention involves antifouling surfaces based on shape memory triggered changes in surface topography. This strategy was found effective for the removal of established biofilms of multiple species. Future studies are needed to understand the underlying mechanism and develop biocompatible polymers for in vivo use. Long-term biofilm control may be possible by employing surface topographies on such polymers to achieve biofilm inhibition and self-cleaning.

What is claimed is:

1. A medical device, comprising a catheter having an inside surface, wherein the inside surface is formed from a shape memory polymer that can transform from a first topography having a first linear pattern to a second topography that is different than said first topography.

2. The device of claim 1, wherein the second topography is a smooth surface.

3. The device of claim 2, wherein the first linear pattern comprises a plurality of linear elements each having a width of 20 micrometers and the linear elements are separated from each other by a width of 20 micrometers.

4. The device of claim 1, wherein the second topography is a second linear pattern having a different orientation than the first linear pattern.

5. The device of claim 1, wherein the shape memory polymer transforms from said first topography to said second topography in response to heat.

6. The device of claim 1, where the linear pattern comprises a plurality of linear elements each having a width of five micrometers and a height of five micrometers, and wherein the linear elements are separated from each other by a width of three micrometers.

7. The device of claim 1, wherein the shape memory polymer comprises t-butyl acrylate (tBA), poly (ethylene glycol)n dimethacrylate (PEGDMA), and photoinitiator 2,2-dimethoxy-2-phenylacetophenone (DMPA).

8. The device of claim 1, wherein the linear pattern forms a spiral on the inside of the catheter.

9. A medical device, comprising a surface formed from a shape memory polymer that can transform from a first topography to a second topography that is different than said first topography, wherein the shape memory polymer is programmed to transform the first topography from having a hexagonal recessive pattern formed from individual elements, each of which singularly forms a hexagon, into the second topography having a flat surface.

10. The device of claim 9, wherein the shape memory polymer transforms from said first topography to said second topography in response to a stimuli selected from the group consisting of heat, pH change, electric current, magnetism, moisture, and light.

11. The device of claim 10, wherein the surface is on the inside of a catheter.

12. The device of claim 11, wherein the shape memory polymer comprises t-butyl acrylate (tBA), poly (ethylene glycol)n dimethacrylate (PEGDMA), and photoinitiator 2,2-dimethoxy-2-phenylacetophenone (DMPA).

* * * * *